US010302569B2

(12) United States Patent
Matsumoto et al.

(10) Patent No.: US 10,302,569 B2
(45) Date of Patent: *May 28, 2019

(54) MICROSCOPE DEVICE AND IMAGE ACQUISITION METHOD

(71) Applicant: HAMAMATSU PHOTONICS K.K., Hamamatsu-shi, Shizuoka (JP)

(72) Inventors: Naoya Matsumoto, Hamamatsu (JP); Koyo Watanabe, Hamamatsu (JP); Hirotoshi Terada, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/858,818

(22) Filed: Dec. 29, 2017

(65) Prior Publication Data

US 2018/0143137 A1    May 24, 2018

Related U.S. Application Data

(63) Continuation of application No. 15/311,912, filed as application No. PCT/JP2015/064160 on May 18, 2015, now Pat. No. 9,891,172.

(30) Foreign Application Priority Data

May 21, 2014 (JP) ................................ 2014-105420

(51) Int. Cl.
  *G01N 21/64* (2006.01)
  *G02B 21/00* (2006.01)
  (Continued)

(52) U.S. Cl.
  CPC ......... *G01N 21/6458* (2013.01); *G01B 9/021* (2013.01); *G01B 11/24* (2013.01);
  (Continued)

(58) Field of Classification Search
  CPC .... G02B 21/26; G02B 21/08; G01N 21/6458; G01N 21/64; G01N 21/6486; G03H 1/0005
  See application file for complete search history.

(56) References Cited

U.S. PATENT DOCUMENTS

| 7,977,625 B2 * | 7/2011 | Schwertner ........ G01B 11/2504 250/252.1 |
| 9,383,573 B2 | 7/2016 | Matsumoto et al. |

(Continued)

FOREIGN PATENT DOCUMENTS

| CN | 100388043 C | 5/2008 |
| EP | 1912060 A1 | 4/2008 |

(Continued)

OTHER PUBLICATIONS

International Preliminary Report on Patentability dated Dec. 1, 2016 for PCT/JP2015/064160.

(Continued)

*Primary Examiner* — Marcus H Taningco
(74) *Attorney, Agent, or Firm* — Drinker Biddle & Reath LLP

(57) ABSTRACT

A microscope apparatus (1A) includes a biological sample table (11) that supports the biological sample (B), an objective lens (12) disposed to face the biological sample table (11), a laser light source (13) that outputs light with which the biological sample (B) is irradiated via the objective lens (12), a shape measurement unit (20) that acquires a surface shape of the biological sample (B), a control unit (40) that generates aberration correction hologram data for correcting an aberration caused by the surface shape of the biological sample (B) on the basis of information acquired in the shape measurement unit (20), a first spatial light modulator (33) to which a hologram based on the aberration correction hologram data is presented and that modulates the light output (Continued)

from the laser light source (31), and a photodetector (37) that detects an intensity of light to be detected (L2) generated in the biological sample (B). Thus, a microscope apparatus and an image acquisition method capable of suppressing a decrease in condensing intensity of irradiation light inside a biological sample and spreading of a condensing shape are realized.

12 Claims, 16 Drawing Sheets

(51) Int. Cl.
    *G02B 27/00* (2006.01)
    *G01B 9/021* (2006.01)
    *G01B 11/24* (2006.01)
    *G02B 21/08* (2006.01)
    *G02B 21/26* (2006.01)
    *G03H 1/00* (2006.01)
    *G02B 21/36* (2006.01)
    *G02B 5/32* (2006.01)

(52) U.S. Cl.
    CPC ......... *G01N 21/64* (2013.01); *G01N 21/6486* (2013.01); *G02B 21/00* (2013.01); *G02B 21/08* (2013.01); *G02B 21/26* (2013.01); *G02B 21/361* (2013.01); *G02B 21/365* (2013.01); *G02B 27/0068* (2013.01); *G03H 1/0005* (2013.01); *G01N 2201/06113* (2013.01); *G02B 5/32* (2013.01); *G03H 2001/005* (2013.01)

(56) References Cited

U.S. PATENT DOCUMENTS

| | | | |
|---|---|---|---|
| 2004/0227101 A1 | 11/2004 | Iketaki et al. | |
| 2006/0203231 A1* | 9/2006 | Uto | G01N 21/47 356/237.2 |
| 2007/0007428 A1* | 1/2007 | Ri | G02B 21/006 250/201.3 |
| 2008/0074739 A1 | 3/2008 | Terada et al. | |
| 2012/0008181 A1 | 1/2012 | Cable et al. | |
| 2017/0082597 A1 | 3/2017 | Matsumoto et al. | |

FOREIGN PATENT DOCUMENTS

| | | |
|---|---|---|
| JP | 2004-239660 A | 8/2004 |
| JP | 2004-341394 A | 12/2004 |
| JP | 2007-033951 A | 2/2007 |
| JP | 2008-051773 A | 3/2008 |
| JP | 2010-075997 A | 4/2010 |
| JP | 2013-034127 A | 2/2013 |
| JP | 2013-160893 A | 8/2013 |
| WO | WO 2013/115383 A1 | 8/2013 |

OTHER PUBLICATIONS

Oscar Azucena, et al., "Wavefront aberration measurements and corrections through thick tissue using fluorescent microsphere reference beacons," Optics Express, vol. 18, No. 16, 2010, pp. 17521-17532.

M.J. Booth, et al., "Aberration correction for confocal imaging in refractive-index-mismatched media," Journal of Microscopy vol. 192, Pt. 2, 1998, pp. 90-98.

Na Ji et al., "Adaptive optics via pupil segmentation, for high-resolution imaging in biological tissues," Nature Methods, vol. 7, No, 2, 2010, pp. 141-147.

Bergin Gjonaj, et al., "Index mismatch aberration correction over long working distances using spatial light modulation.," Applied Optics vol. 51, No. 33, 2012, pp. 80341-8049.

P.N. Marsh, et al., "Practical implementation of adaptive optics in multiphoton microscopy," Optics Express vol. 11 No. 10, 2003, pp. 1123-1130.

U.S. Office Action dated Feb. 5, 2018 that issued in U.S. Appl. No. 15/312,054 including Double Patenting Rejections on pp. 2-4.

* cited by examiner

*Fig.7*
(a)
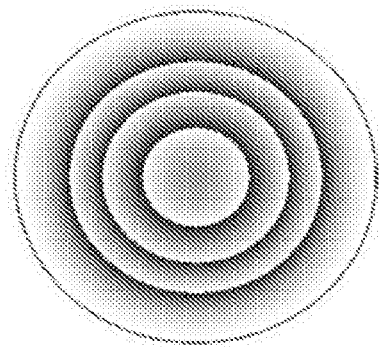
(b)
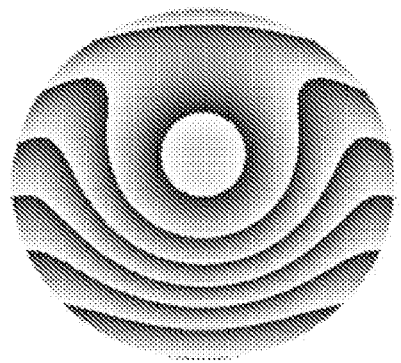

*Fig.12*
(a)
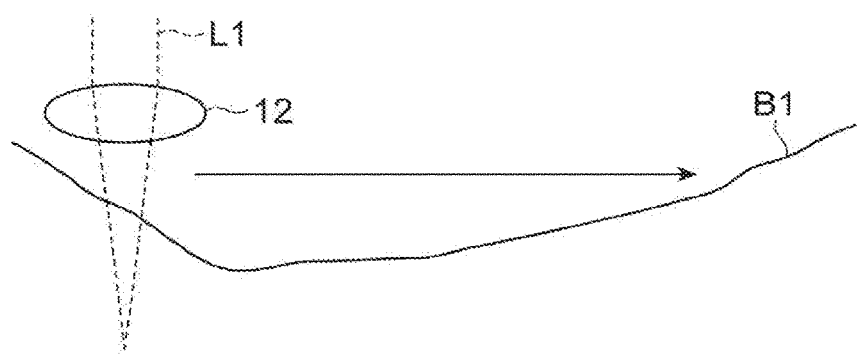
(b)
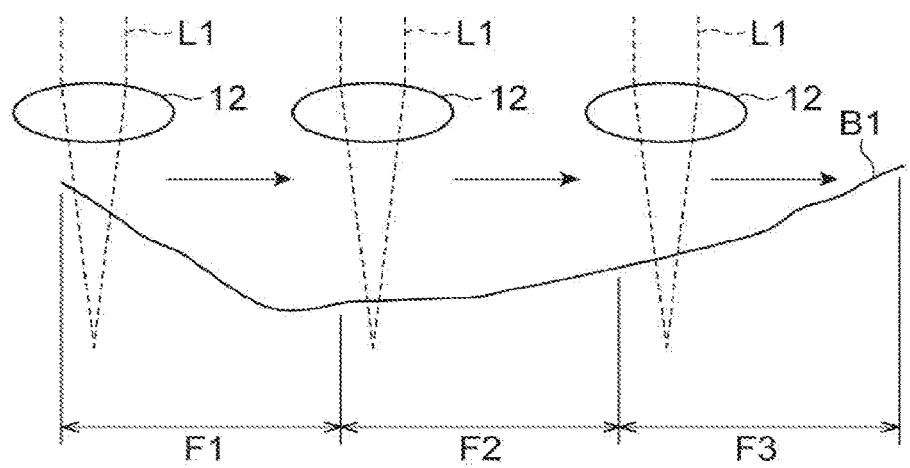

MICROSCOPE DEVICE AND IMAGE ACQUISITION METHOD

TECHNICAL FIELD

One aspect of the present invention relates to a microscope apparatus and an image acquisition method.

BACKGROUND ART

Patent Literature 1 describes a technology regarding a microscope capable of performing aberration correction. In this microscope, a sample is irradiated with excitation light, fluorescence generated in the sample is split and condensed, and a condensing image is captured by a camera. A spot of the condensing image is a diffraction limit image when there is no aberration, and has a shape with a distortion when there is an aberration. Therefore, in this microscope, wavefront aberration correction is applied to attempt to improve a spot shape. Accordingly, a plurality of aberration conditions corresponding to a plurality of spot shapes are stored, selected, and applied to achieve high speed.

CITATION LIST

Patent Literature

[Patent Literature 1] Japanese Unexamined Patent Publication No. 2013-160893

SUMMARY OF INVENTION

Technical Problem

A characteristic of the spatial light modulator is that various aberrations can be corrected by controlling a wavefront. For example, in a laser scanning microscope, there is a problem in that a spherical aberration is generated due to mismatch in refractive index between an observation target and a surrounding medium (for example, air, water, silicone oil, or oil), and a condensing point of the irradiation light extends in an optical axis direction inside the observation target, but the extension of the condensing point inside the observation target can be suppressed by controlling the wavefront of the irradiation light using a spatial light modulator and correcting the spherical aberration. Since a fine image can be obtained by such aberration correction, such a microscope is preferably used, for example, to obtain an internal observation image of a biological sample, such as a blood vessel image of a brain.

In many cases, however, a surface of the biological sample is not flat. Accordingly, an aberration caused by a surface shape of the biological sample occurs, in addition to the above-described aberration. For example, when a fish such as a zebrafish is observed as a biological sample, a surface shape of the fish can be regarded as substantially a cylindrical shape, and an astigmatism aberration occurs due to the cylindrical shape. Further, for example, a biological sample such as a cell sample includes a blood vessel, a cell tissue or the like. Accordingly, there are substances with different refractive indexes such as red blood cells or lipids. Therefore, an aberration occurs inside the biological sample. When irradiation light is under an influence of aberration, there is a problem in that a condensing intensity of the irradiation light is weakened inside the biological sample or a condensing shape spreads.

One aspect of the present invention has been made in view of such problems, and an object thereof is to provide a microscope apparatus and an image acquisition method capable of suppressing a decrease in condensing intensity of irradiation light inside a biological sample and spreading of a condensing shape.

Solution to Problem

To solve the problems described above, a microscope apparatus according to one aspect of the present invention is an apparatus for acquiring an image of a biological sample, and includes a biological sample table for supporting the biological sample; an objective lens disposed to face the biological sample table; a light source for outputting light with which the biological sample is irradiated via the objective lens; a shape acquisition unit for acquiring information on at least one of a surface shape of the biological sample and a structure directly under the surface of the biological sample; a hologram generation unit for generating aberration correction hologram data for correcting an aberration caused by the at least one on the basis of the information acquired by the shape acquisition unit; a spatial light modulator to which a hologram based on the aberration correction hologram data is presented and for modulating the light output from the light source; a photodetector for detecting an intensity of light generated in the biological sample and outputs a detection signal; and an image generation unit for generating an image of the biological sample on the basis of the detection signal.

Further, an image acquiring method according to one aspect of the present invention is a method for acquiring an image of a biological sample and includes a step of acquiring information on at least one of a surface shape of the biological sample supported by a biological sample table facing an objective lens and a structure directly under the surface of the biological sample (shape acquisition step); a step of generating aberration correction hologram data for correcting an aberration caused by the at least one on the basis of the information acquired in the shape acquisition step (hologram generation step); a step of presenting a hologram based on the aberration correction hologram data to a spatial light modulator, modulating the light output from a light source using the spatial light modulator, and irradiating the biological sample with light after modulation (light irradiation step); a step of detecting an intensity of light generated in the biological sample and outputting a detection signal (light detection step); and a step of generating an image of the biological sample on the basis of the detection signal (image generation step).

In the microscope apparatus and the image acquisition method, information on at least one of the surface shape of the biological sample and the structure directly under the surface of the biological sample is acquired. The aberration correction hologram data for correcting an aberration is generated on the basis of that information. Further, the irradiation light is modulated by the hologram based on the data. Accordingly, since an aberration caused by at least one of the surface shape of the biological sample and the structure directly under the surface of the biological sample is preferably corrected, it is possible to suppress a decrease in condensing intensity of the irradiation light inside the biological sample and spreading of the condensing shape.

Advantageous Effects of Invention

According to the microscope apparatus and the image acquisition method according to an aspect of the present invention, it is possible to suppress a decrease in condensing intensity of the irradiation light inside the biological sample and spreading of a condensing shape.

BRIEF DESCRIPTION OF DRAWINGS

FIGS. 7(a) and 7(b) are diagrams illustrating a wavefront obtained using backpropagation analysis, in which a phase is indicated by shading.

FIGS. 12(a) and 12(b) are diagrams illustrating a state of scanning of the first modification example.

DESCRIPTION OF EMBODIMENTS

Figure 1:
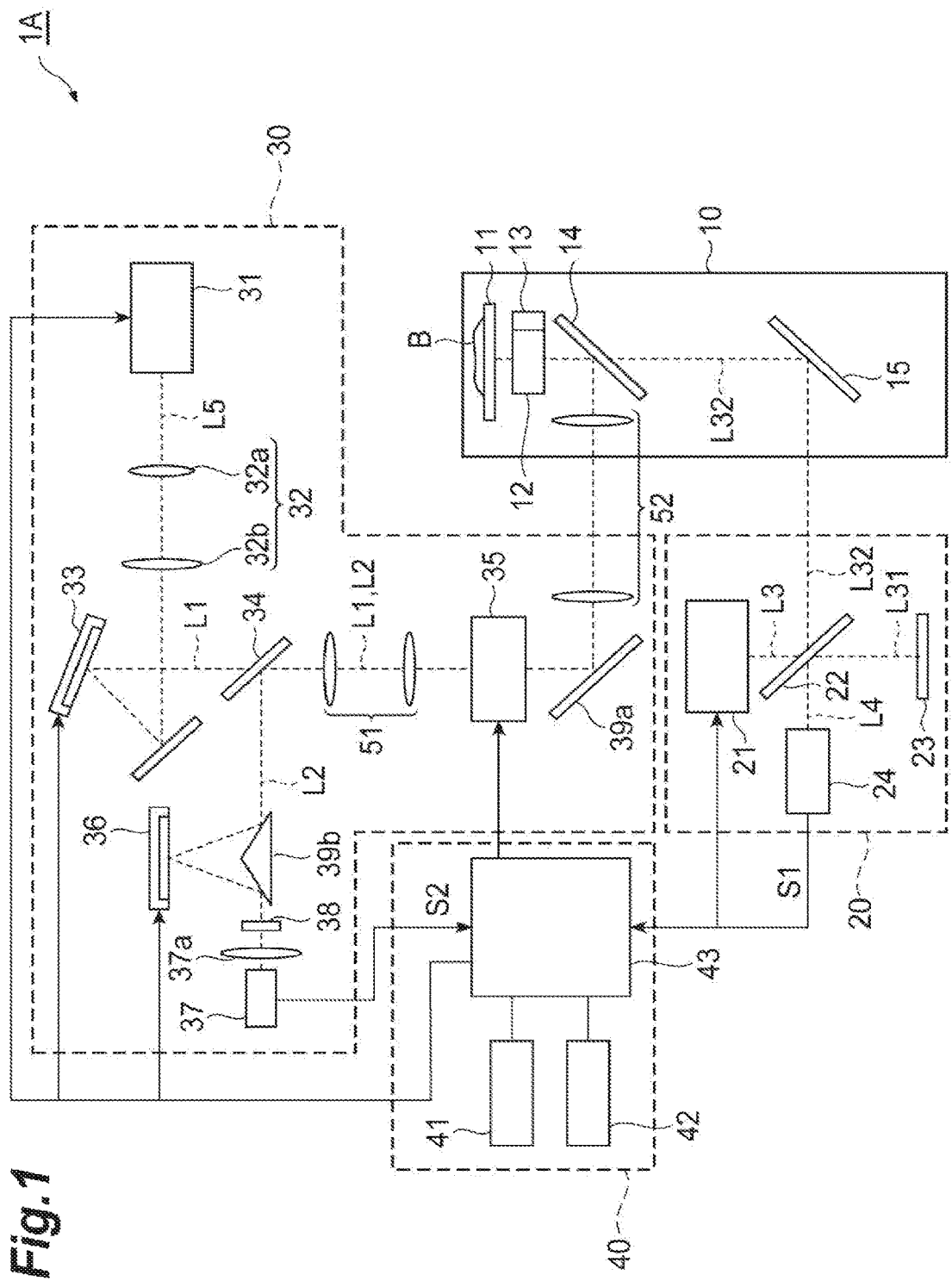
FIG. 1 is a diagram illustrating a configuration of a microscope apparatus according to a first embodiment.

Hereinafter, embodiments of a microscope apparatus and an image acquisition method according to an aspect of the present invention will be described with reference to the accompanying drawings. In the description of the drawings, the same elements are denoted with the same reference numerals, and repeated description will be omitted.

First Embodiment

FIG. 1 is a diagram illustrating a configuration of a microscope apparatus 1A according to an embodiment of one aspect of the present invention. The microscope apparatus 1A is an apparatus for acquiring an image of a biological sample B. The microscope apparatus 1A includes a microscope unit 10, a shape measurement unit 20, an image acquisition unit 30, and a control unit 40, as illustrated in FIG. 1.

The microscope unit 10 irradiates the biological sample B with irradiation light L1 from a shape measurement unit 20 and an image acquisition unit 30, which will be described below, and outputs light to be detected L2 from the biological sample B to each of the shape measurement unit 20 and the image acquisition unit 30. The light to be detected L2 is reflected light of the irradiation light L1, harmonics of the irradiation light L1, or fluorescence excited by the irradiation light L1. The microscope unit 10 includes a biological sample table 11, an objective lens 12, an objective lens moving mechanism 13, and a beam splitter 14.

The biological sample table 11 is a plate-like member for supporting the biological sample B (or a vessel that accommodates the biological sample B). The biological sample table 11 is formed of, for example, a material that transmits the irradiation light L1 and the light to be detected L2, such as glass or plastic. The biological sample table 11 is, for example, a glass slide, a bottomed dish, or a microplate. In this embodiment, the irradiation light L1 is radiated to a back surface of the biological sample table 11, transmitted through the biological sample table 11, and radiated to the biological sample B. Further, the light to be detected L2 from the biological sample B is transmitted through the biological sample table 11 and output from the back surface of the biological sample table 11.

The objective lens 12 is disposed to face the biological sample table 11, and condenses the irradiation light L1 on the inside of the biological sample B. Further, the objective lens 12 collects the light to be detected L2 from the biological sample B.

Although a common objective lens is used for the objective lens for the irradiation light L1 and the objective lens for the light to be detected L2 in this embodiment, the objective lens for the irradiation light L1 and the objective lens for the light to be detected L2 may be individually provided. For example, an objective lens having a high numerical aperture (NA) may be used for the irradiation light L1 and locally focused by aberration correction. Further, an objective lens having a large pupil may be used for the light to be detected L2 to extract a larger amount of light. The objective lens for the irradiation light L1 and the objective lens for the light to be detected L2 may be arranged so that the biological sample B is interposed therebetween and transmitted light in the biological sample B of the irradiation light L1 may be acquired as the light to be detected L2.

The objective lens moving mechanism 13 is a mechanism for moving the objective lens 12 in the optical axis direction of the irradiation light L1. The objective lens moving mechanism 13 includes a stepping motor, a piezo-actuator, or the like.

The beam splitter 14 divides and combines an optical path between the microscope unit 10 and the image acquisition unit 30 and an optical path between the microscope unit 10 and the shape measurement unit 20. Specifically, the beam splitter 14 reflects the irradiation light L1 reaching the microscope unit 10 from the image acquisition unit 30, toward the objective lens 12. Further, the beam splitter 14 reflects the light to be detected L2 collected by the objective lens 12, toward the image acquisition unit 30. On the other hand, the beam splitter 14 transmits light L32 from the shape measurement unit 20 and reflected light of the light L32 in the biological sample B. The beam splitter 14 may include, for example, a half mirror or a dichroic mirror. The microscope unit 10 further includes a reflective mirror 15 that changes an optical axis direction of the light L32.

The shape measurement unit 20 is a shape acquisition unit in this embodiment. The shape measurement unit 20 includes a detector 24, and is optically coupled to the objective lens 12. The shape measurement unit 20 acquires information on a shape with a refractive index distribution of the biological sample B, that is, information on a surface shape of the biological sample B (a shape according to a refractive index difference due to the biological sample B and the surrounding (air)). The shape measurement unit 20 may be, for example, an interference light measurement unit that measures the surface shape of the biological sample B using a Michelson interferometer. In this case, the shape measurement unit 20 includes a coherent light source 21, a beam splitter 22, a reference light mirror 23, and a detector 24, as illustrated in FIG. 1.

The coherent light source 21 generates coherent light L3 with which the biological sample B is irradiated. The coherent light source 21 preferably includes, for example, a semiconductor laser element.

The beam splitter 22 causes the coherent light L3 from the coherent light source 21 to separate into reference light L31 and light L32 directed to the microscope unit 10. Further, the beam splitter 22 reflects the reference light L31 reflected by the reference light mirror 23 and transmits reflected light from the surface of the biological sample B of the light L32. Accordingly, the beam splitter 22 combines the lights to generate interference light L4. The interference light L4 is input to the detector 24. The reference light mirror 23 may be configured to be movable with respect to the optical axis direction of the reference light L31 or may be fixed.

The detector 24 detects the interference light L4 combined by the beam splitter 22 and outputs a detection signal S1. The detector 24 includes a two-dimensional photodetector such as a CCD image sensor or a CMOS image sensor.

The shape measurement unit is not limited to the configuration of this embodiment. For example, the shape measurement unit may use an interference measurement scheme such as a Mirau type or a Linnik type. Alternatively, the shape measurement unit may include a confocal reflectance microscope or may include a common path interferometer. According to such a microscope, it is possible to preferably measure the surface shape of the biological sample B using focusing information. Further, the shape measurement unit may use evanescent light. Accordingly, shape recognition such as recognition as to whether or not the biological sample B is grounded on the biological sample table 11 is facilitated.

The image acquisition unit 30 detects the light to be detected L2 from the biological sample B to generate an image. Hereinafter, an example of a fluorescence optical system in a case in which the light to be detected L2 is fluorescence from the biological sample B will be described, but the irradiated light generation unit is not limited thereto, and a reflective optical system in a case in which the light to be detected L2 is reflected light from the biological sample B or a transmissive optical system in a case in which the light to be detected L2 is transmitted light from the biological sample B may be used. The image acquisition unit 30 of this embodiment includes a laser light source 31, a beam expander 32, a first spatial light modulator (SLM) 33, a dichroic mirror 34, an optical scanner 35, a second spatial light modulator (SLM) 36, a detector 37, and a filter 38.

The laser light source 31 is a light irradiation unit in this embodiment, and irradiates the biological sample B with light L5 via the objective lens 12. The laser light source 31 is a light source that outputs the light L5 with which the biological sample B is irradiated via the objective lens 12. The laser light source 31 is optically coupled to the objective lens 12. The light L5 is, for example, laser light including an excitation wavelength of the biological sample B. The laser light source 31 includes, for example, a semiconductor laser element. The beam expander 32 includes, for example, a plurality of lenses 32a and 32b arranged side by side on an optical axis of the light L5, and adjusts a size of a cross-section perpendicular to the optical axis of the light L5.

A first spatial light modulator 33 is optically coupled to the laser light source 31. The first spatial light modulator 33 presents a hologram including an aberration correction hologram for correcting an aberration caused by the surface shape of the biological sample B. The first spatial light modulator 33 modulates the light L5 from the laser light source 31 to generate the irradiation light L1 with which the biological sample B is irradiated. The surface shape of the biological sample B is measured by the shape measurement unit 20 described above. The first spatial light modulator 33 may be of a phase modulation type or of an amplitude (intensity) modulation type. Further, the first spatial light modulator 33 may be either of a reflection type or of a transmission type. The aberration correction hologram will be described in detail below.

The dichroic mirror 34 transmits one of the irradiation light L1 from the first spatial light modulator 33 and the light to be detected L2 from the microscope unit 10 and reflects the other. In the example illustrated in FIG. 1, the dichroic mirror 34 transmits the irradiation light L1 and reflects the light to be detected L2.

The optical scanner 35 scans an irradiation position of the irradiation light L1 in the biological sample B by moving an optical axis of the irradiation light L1 within a plane perpendicular to the optical axis of the irradiation light L1. The optical scanner 35 includes, for example, a galvanometer mirror, a resonant mirror, a MEMS mirror, or a polygon mirror. Further, the light to be detected L2 from the biological sample B is detected through the optical scanner 35. Thus, it is possible to match the optical axis of the irradiation light L1 with the optical axis of the light to be detected L2.

The second spatial light modulator 36 is optically coupled to the objective lens 12 and the detector 37. The second spatial light modulator 36 presents an aberration correction hologram for correcting aberration caused by the surface shape of the biological sample B. The second spatial light modulator 36 modulates the light to be detected L2 from the dichroic mirror 34. The surface shape of the biological sample B is measured by the shape measurement unit 20 described above. The second spatial light modulator 36 may be of a phase modulation type or may be of an amplitude (intensity) modulation type. Further, the second spatial light modulator 36 may be of either a reflection type or a transmission type.

Further, when a pinhole is disposed at a preceding stage from the detector 37, it is preferable for a hologram for condensing the light to be detected L2 on the pinhole to be presented to the second spatial light modulator 36, in addition to the aberration correction hologram. Thus, it is possible to obtain a confocal effect. When the light to be detected L2 such as fluorescence generated from the biological sample B is detected using a multi-photon absorption effect such as two-photon absorption, a hologram for condensing the light to be detected L2 on the detector 37 is combined with the aberration correction hologram and presented to the second spatial light modulator 36, such that the confocal effect can be obtained. The aberration correction hologram will be described in detail below.

The detector 37 is an light detection unit of this embodiment. The detector 37 is optically coupled to the objective lens 12. The detector 37 detects a light intensity of the light to be detected L2 that is output via the objective lens 12 from the biological sample B, and outputs a detection signal S2. The detector 37 may be a point sensor such as a photomultiplier tube (PMT), a photodiode, or an avalanche photodiode. Alternatively, the detector 37 may be an area image sensor such as a CCD image sensor, a CMOS image sensor, a multi-anode PMT, or a photodiode array. A condensing lens 37a may be disposed directly before the detector 37.

The filter 38 is disposed on an optical axis between the dichroic mirror 34 and the detector 37. The filter 38 cuts a wavelength of the irradiation light L1 and a wavelength of fluorescence or the like unnecessary for observation from the light that is input to the detector 37. The filter 38 may be disposed at a preceding stage or a subsequent stage from the condensing lens 37a.

The image acquisition unit 30 of this embodiment further includes a mirror 39a and a reflective member 39b, in addition to the above configuration. The mirror 39a bends the optical axis of the irradiation light L1 and the light to be detected L2 in order to optically couple the optical scanner 35 to the beam splitter 14 of the microscope unit 10. The reflective member 39b is a prism having two reflective surfaces and is disposed to face the second spatial light modulator 36. The reflective member 39b reflects the light to be detected L2 from the dichroic mirror 34 toward the second spatial light modulator 36 at one of the reflective surfaces, and reflects the light to be detected L2 from the second spatial light modulator 36 toward the detector 37 at the other reflective surface.

When a distance between the objective lens 12 and the first spatial light modulator 33 is long, at least one 4f optical system may be provided on an optical axis of the irradiation light L1 and the light to be detected L2. As an example, two 4f optical systems 51 and 52 are illustrated in FIG. 1. The 4f optical systems 51 and 52 serve to transfer a wavefront of the irradiation light L1 generated in the first spatial light modulator 33 to a rear-side focus point of the objective lens 12. The 4f optical system may include a telecentric relay optical system. Further, when the objective lens 12 is very close to the first spatial light modulator 33, the 4f optical system may be omitted.

The control unit 40 includes a processor. The control unit 40 controls the microscope unit 10, the shape measurement unit 20, and the image acquisition unit 30. For example, the control unit 40 controls a position in the optical axis direction of the objective lens 12 using the objective lens moving mechanism 13 in the microscope unit 10. Further, the control unit 40 moves the biological sample table 11 that supports the biological sample B in a direction crossing the optical axis direction. Further, the control unit 40 performs control of the coherent light source 21, the detector 24, and the reference light mirror 23 of the shape measurement unit 20. Further, the control unit 40 controls the laser light source 31, the first spatial light modulator 33, the optical scanner 35, the second spatial light modulator 36, and the detector 37 of the image acquisition unit 30. The control unit 40 of this embodiment includes an input device 41 such as a mouse or a keyboard, a display device (display) 42, and a computer 43.

Further, the control unit 40 constitutes a portion of the shape acquisition unit in this embodiment. The control unit 40 is electrically coupled to the detector 24 of the shape measurement unit 20. The control unit 40 receives the detection signal S1 that is output from the detector 24 of the shape measurement unit 20. The control unit 40 acquires information on the surface shape of the biological sample B using a method using a Fourier transform or a $\lambda/4$ phase-shifting interferometry on the basis of the detection signal S1. Further, the control unit 40 is a hologram generation unit in the embodiment. The control unit 40 generates aberration correction hologram data for correcting aberration caused by the surface shape of the biological sample B on the basis of the obtained information. The aberration correction hologram data is provided to the first spatial light modulator 33 and the second spatial light modulator 36.

Further, the control unit 40 is an image generation unit in this embodiment. The control unit 40 generates an image regarding the biological sample B on the basis of the detection signal S2 from the detector 37 and information, on an irradiation position of the optical scanner 35. The generated image is displayed on the display device 42. The control unit 40 may realize a function of controlling the respective units, a function as the shape acquisition unit, a function as the hologram generation unit, and a function as an image generation unit using the same processor or may realize the functions using different processors.

Figure 2:
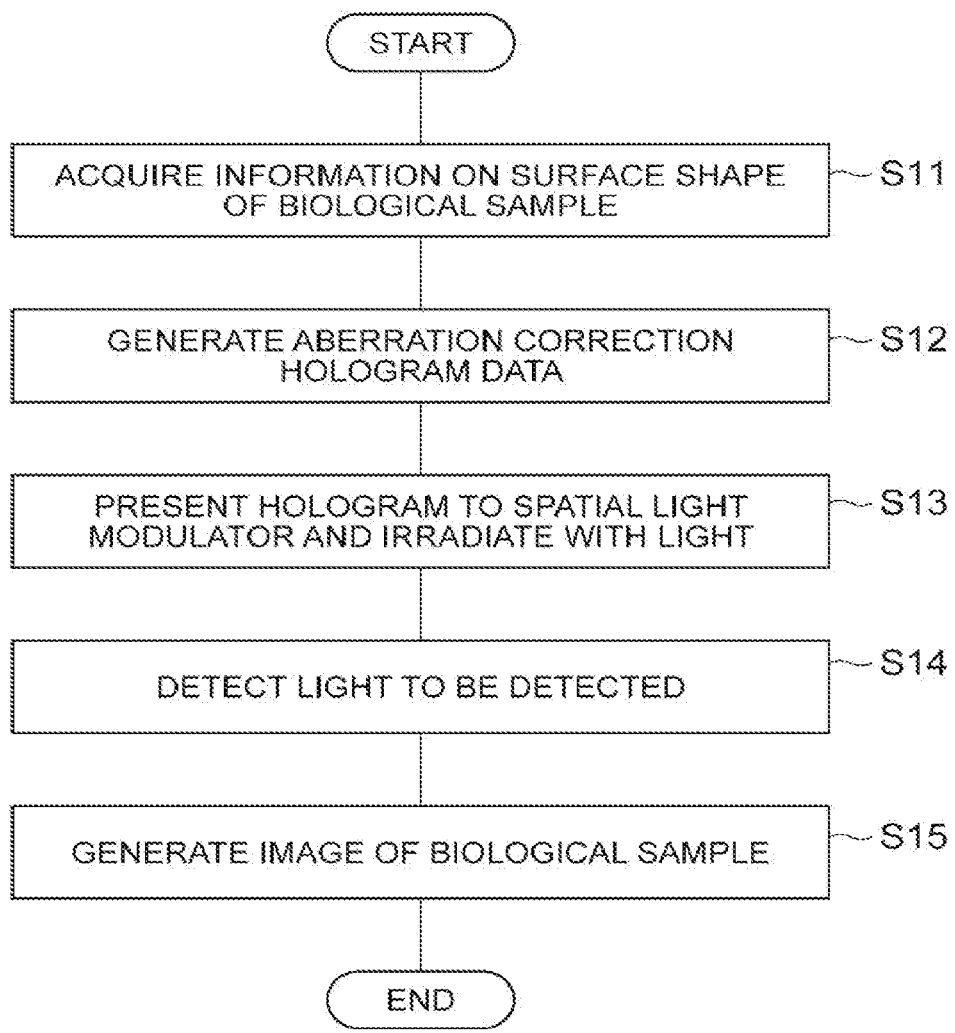
FIG. 2 is a flowchart illustrating an operation of a microscope apparatus.

FIG. 2 is a flowchart illustrating an operation of the microscope apparatus 1A described above. An image acquisition method according to this embodiment will be described with reference to FIG. 2.

First, the biological sample B is placed on the biological sample table 11. Then, the light L3 is output from the light source 21 of the shape measurement unit 20, and the detector 24 detects the interference light L4 of the reflected light from the surface of the biological sample B and the reference light L31. Thus, an interference pattern is observed on the surface of the biological sample B. In the control unit 40, information on the surface shape of the biological sample B is acquired on the basis of the interference pattern (shape acquisition step S11).

Subsequently, aberration correction hologram data for correcting the aberration caused by the surface shape of the biological sample B is generated by the control unit 40 on the basis of the information acquired in the shape acquisition step S11 (hologram generation step S12). Subsequently, the hologram based on the aberration correction hologram data is presented to the first spatial light modulator 33 and the second spatial light modulator 36. The light L5 emitted from the laser light source 31 is modulated by the first spatial light modulator 33, and the biological sample B is irradiated with the irradiation light L1 after modulation (light irradiation step S13).

Subsequently, the detector 37 detects the intensity of the light to be detected L2 generated in the biological sample B (light detection step S14). In this case, the light to be detected L2 is modulated by the second spatial light modulator 36 and then input to the detector 37. In this embodiment, the light irradiation step S13 and the light detection step S14 are repeatedly performed (or simultaneously continuously) while scanning the irradiation light L1 using the optical scanner 35. Then, the image of the biological sample B is generated on the basis of the detected information in the light detection step S14 in the control unit 40 (image generation step S15).

Effects obtained by the microscope apparatus 1A and the image acquisition method of this embodiment including the above configuration will be described.

In many cases, the surface of the biological sample B is not flat. Therefore, an aberration caused by the surface shape of the biological sample B occurs. For example, if a surface shape of a fish is assumed to be substantially cylindrical in shape when a fish such as a zebrafish is observed as the biological sample B, a strong astigmatism aberration occurs when the irradiation light L1 in a condensing process passes through the surface. When a numerical aperture (NA) of the objective lens 12 is small or observation is performed at a shallow position in the biological sample B, an influence thereof is less, but when the numerical aperture (NA) is great or the observation is performed at a deep position, the influence cannot be neglected. There is a problem in that a condensing intensity of the irradiation light L1 inside the biological sample B becomes weak or a condensing shape spreads when the irradiation light L1 is under an influence of such an aberration. Accordingly, for example, degradation of resolution due to extension of an excitation region, a decrease in fluorescence intensity, and a decrease in a signal to noise ratio (SN ratio) due to an increase in background noise occur.

Figure 3:
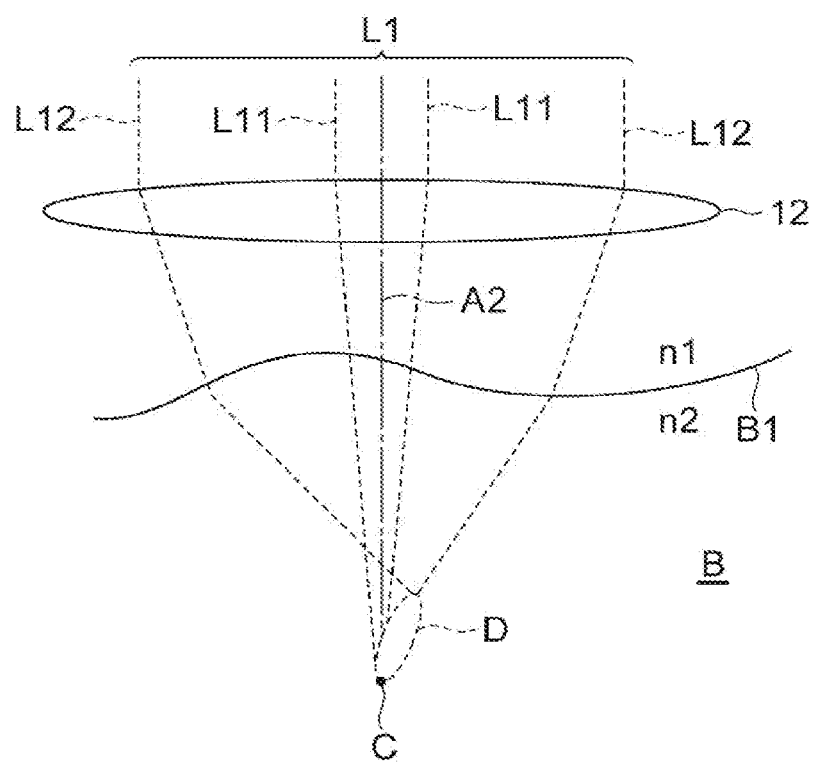
FIG. 3 is a diagram schematically illustrating a state of generation of an aberration.

FIG. 3 is a diagram schematically illustrating a state of occurrence of an aberration. In FIG. 3, a curve B1 represents a boundary between the surface of the biological sample B, that is, the biological sample B and outside thereof. It is assumed that a refractive index outside of the biological sample B is n1 and a refractive index of the inside of the biological sample B is n2 (≠n1). The irradiation light L1 is condensed on the inside (directly under the surface) of the biological sample B by the objective lens 12. In this case, light L11 that passes through the vicinity of an optical axis A2 of the objective lens 12 in the irradiation light L1 goes straight toward the condensing point C under almost no influence from the surface shape of the biological sample B. On the other hand, light L12 passing through a position apart from the optical axis A2 of the objective lens 12 in the irradiation light L1 is refracted under the influence of the surface shape of the biological sample B and deviates from the condensing point C. Due to this phenomenon, a condensing intensity of the irradiation light L1 inside the biological sample B becomes weak and a condensing image D spreads.

In the microscope apparatus 1A and the image acquisition method of this embodiment, information on the surface shape of the biological sample B is acquired. On the basis of the information, aberration correction hologram data for correcting an aberration is generated. Further, the irradiation light L1 is modulated by a hologram based on the data. Thus, since the aberration caused by the surface shape of the biological sample B is preferably corrected, it is possible to suppress a decrease in the condensing intensity of the irradiation light L1 inside the biological sample B and spreading of the condensing image D.

Further, as in this embodiment, the hologram based on the aberration correction hologram data may be presented to the second spatial light modulator 36, and the light to be detected L2 generated in the biological sample B may be modulated by the second spatial light modulator 36. Thus, the influence of the aberration caused by the surface shape of the biological sample B on the light to be detected L2 is corrected, and accordingly, when confocal using a pinhole is performed, the light to be detected L2 passing through the pinhole increases such that a clearer image of the biological sample B can be obtained.

Figure 4:
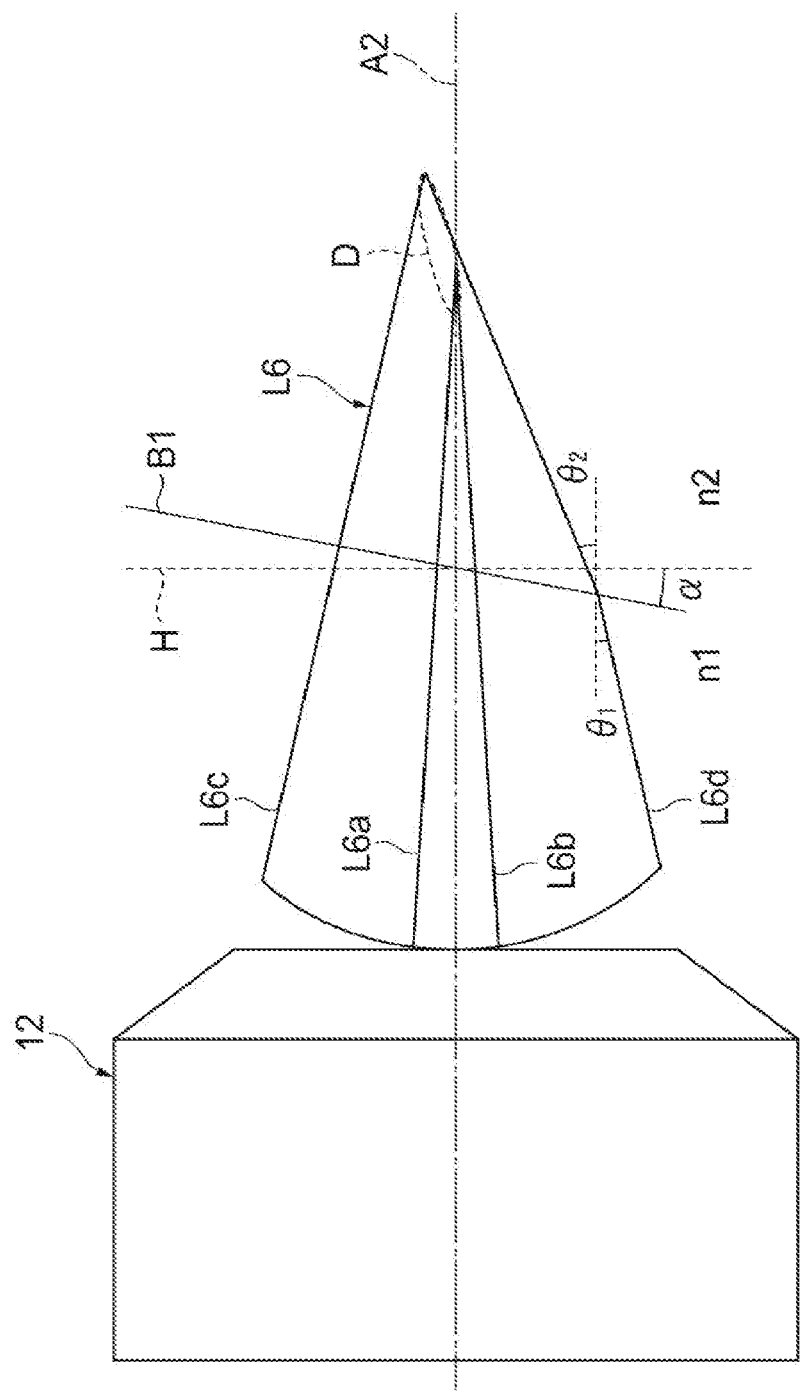
FIG. 4 conceptually illustrates a state of irradiation light when a boundary between a biological sample and outside thereof is inclined from a plane perpendicular to an optical axis in a case in which irradiation light that is plane waves not subjected to aberration correction is condensed by an objective lens.

Here, a method of designing the aberration correction hologram will be described in detail. FIG. 4 conceptually illustrates a state of irradiation light L6 when a boundary B1 between the biological sample B and outside thereof is inclined by an angle $\alpha$ from a plane H perpendicular to the optical axis A2 in a case in which the irradiation light L6 that is plane waves not subjected to the aberration correction is condensed by the objective lens 12. Here, lights L6a and L6b in FIG. 4 are rays passing through the vicinity of a center of the objective lens 12 and are referred to as paraxial rays. Further, lights L6c and L6d in FIG. 4 are rays passing through the vicinity of an edge of the objective lens 12, and are referred to as outer peripheral rays.

When the rays pass through a boundary between the biological sample B and outside thereof, a relationship between an incidence angle $\theta_1$ and an output angle $\theta_2$ of the rays with respect to the boundary B1 is obtained using Snell's law expressed by the following Equation (1).

[Math. 1]

$$\sin(\theta_1 \pm \alpha) = n_2 \sin(\theta_2 \pm \alpha) \quad (1)$$

Since the incidence angle is small for the paraxial rays, the amount of change in the incidence angle and the output angle is small. On the other hand, since the incidence angle is large for the outer peripheral rays, the amount of change in the incidence angle and the output angle is large. Further, since the boundary B1 is inclined with respect to a plane perpendicular to the optical axis A2, the paraxial rays and the outer peripheral rays do not overlap on the optical axis. Accordingly, various aberrations occur and, as a result, the condensing image becomes a distorted image that is different from a diffraction limit image.

Figure 5:
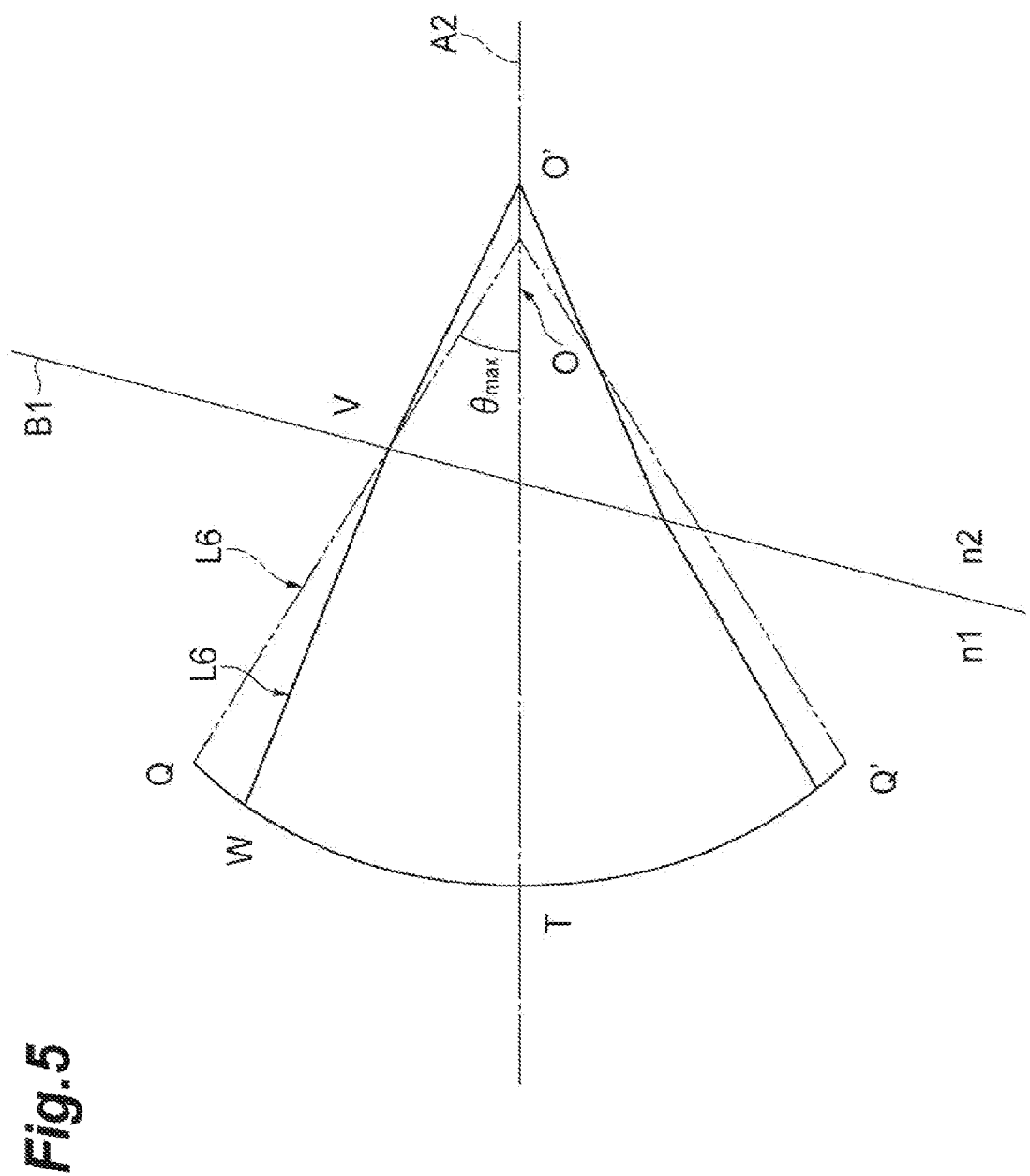
FIG. 5 is a diagram illustrating a method of calculating a wavefront for concentrating rays on any point on an optical axis.

FIG. 5 is a diagram illustrating a method of calculating a wavefront so that rays are concentrated on any point O' on the optical axis A2. An arc Q, Q' is a wavefront after the plane waves pass through the objective lens 12 with a focal length f and, for example, is a spherical crown with a certain radius. If there is no biological sample B, the irradiation light L6A is condensed on another point O on the optical axis A2, as indicated by a two-dot chain line in FIG. 5. Here, an angle $\theta_{max}$ between a line segment OQ (or OQ') and a line segment OT is expressed by the following Equation (2). Here, NA is a numerical aperture of the objective lens 12. Further, T is an intersection of the arc Q, Q' and the optical axis A2.

[Math. 2]

$$\theta_{max} = \sin^{-1}(NA/n1) \quad (2)$$

The rays of the irradiation light L6A are input to the objective lens 12 from the left on the paper surface, and proceed to the right of the paper surface as convergent light. This direction is defined as a positive propagation direction. For example, an optical path from the point O' to a point W on an arc QQ' via a point V on the boundary B1 is obtained through backpropagation. In this embodiment, for example, the optical path is obtained through backpropagation using a method such as backward ray tracing, wavefront propagation, and electromagnetic field analysis to be described below.

<Backward Ray Tracing>

In this embodiment, in a previous step of optical path calculation, a structure of the biological sample B is recognized using interference measurement. Therefore, a refractive index distribution in the biological sample B is estimated from the structure of the biological sample B, and the boundary B1 of the refractive index is obtained. The boundary B1 of this refractive index is subjected to polynomial approximation or map conversion so that the position can be specified.

Then, a path along which rays reach a point W on the arc QQ' from the point O' via the point V on the refractive index boundary B1' and an optical path length are determined. If the rays from the point O' propagate back, the rays reach the point V on the refractive index boundary B1. The point V is obtained by the above-described polynomial approximation or the like. The rays are refracted at the point V using Snell's law due to a refractive index difference before and after the boundary B1. In this embodiment, since the boundary B1 that is not uniform (that has irregular unevenness) is assumed, a three-dimensional Snell's law using a vector and a cross product as shown in Equation (3) below is applied.

[Math. 3]

$$n_1 m \times VW = n_2 \cdot m \times O'V \quad (3)$$

Here, × in Equation (3) denotes a cross product. Further, in Equation (3), m is a normal vector at the point V, and VW and O'V are direction vectors after boundary passage and before boundary passage. After refraction, the rays propagate back again to the point W on the arc QQ'. Thus, the optical path length L is calculated by examining the optical path from the point O' to the point W. The optical path length L is determined using, for example, Equation (4) below.

[Math. 4]

$$L = n_1 |VW| + n_2 |O'V| \quad (4)$$

The above calculation is performed on a plurality of rays to obtain the optical path lengths of all the rays reaching the spherical crown. A phase difference is obtained through the optical path difference from the optical path length, and a pattern for eliminating this phase difference becomes an aberration correction pattern, that is, aberration correction hologram data. In practice, since there are a plurality of boundaries B1 of the refractive index, the rays may be refracted at each boundary B1 of the refractive index and traced. In this case, Equation (4) is changed.

<Wavefront Propagation>

Using Fresnel diffraction, Fresnel-Kirchhoff diffraction, or the like, rays gradually propagate back from a position at which the rays condense (point O') to the objective lens 12. In this case, the calculation is performed by adding the boundary B1 of the refractive index to the propagation. This method may be combined with the backward ray tracing described above or electromagnetic field analysis to be described below. For example, reverse ray tracing may be performed on a portion other than the boundary B1 of the refractive index, and wavefront propagation may be performed on a portion including the boundary B1 of the refractive index. Thus, it is possible to reduce a calculation load.

<Electromagnetic Field Analysis>

Using a Finite-Difference Time-Domain (FDTD) method or a Rigorous Coupled-Wave Analysis (RCWA) method, analysis is performed from a point O' at which condensing is desired to the objective lens 12. In this case, the boundary B1 of the refractive index is added to boundary conditions. This method may be combined with the above-described backward ray tracing or wavefront propagation.

Figure 6:
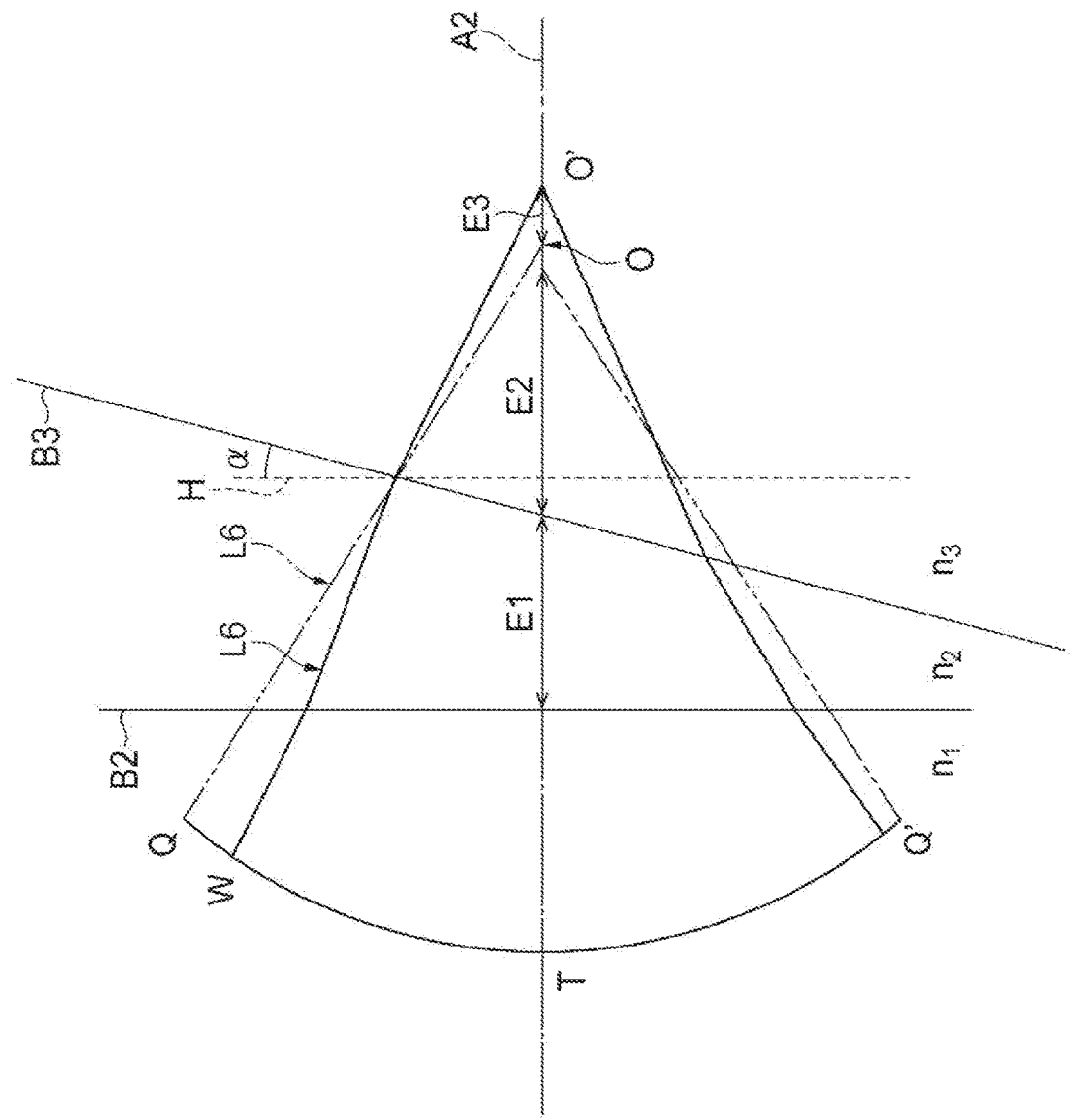
FIG. 6 schematically illustrates a case in which there is a boundary between two refractive indexes.

Conversely propagation analysis using each method described above is applicable even when there are two boundaries of the refractive index. FIG. 6 schematically illustrates a case where there are two refractive index boundaries B2 and B3. The boundary B2 is assumed to be perpendicular to the optical axis. Further, an angle between a plane H perpendicular to the optical axis A2 and the boundary B3 is a. The refractive index outside of the boundary B2 is n1, the refractive index between the boundary B2 and the boundary B3 is n2, and the refractive index inside of the boundary B3 is n3.

FIGS. 7(a) and 7(b) are diagrams illustrating the wavefront obtained using the backpropagation analysis in such a case, and a phase is indicated by shading. FIG. 7 is represented using a technology called phase folding. FIG. 7(a) illustrates a wavefront obtained when α=0°. Further, FIG. 7(b) illustrates a wavefront obtained when α=0.3°. In the calculation of the wavefronts, n1=1, n2=1.33, and n3=1.38. In this case, n1 simulates air, n2 simulates water, n3 simulates a cell. It is assumed that there is a cover glass at the boundary B2 between n1 and n2, but an aberration caused by the cover glass is corrected using a glass correction function of the objective lens 12.

A region sandwiched between the boundary B2 and the boundary B3 on the optical axis (that is, a region sandwiched between the cover glass and the cell) is filled with, for example, phosphate buffered saline. A distance E1 between the boundary B2 and the boundary B3 on the optical axis is, for example, 30 μm. Further, a magnification of the objective lens 12 is 40, a numerical aperture (NA) is 0.75, a distance E2 between the point O and the boundary B3 on the optical axis is 300 μm, and a distance E3 between the point O and the point O' is 80 μm. In the above conditions, a coma aberration and an astigmatism aberration are included in the wavefront, in addition to the spherical aberration. As illustrated in FIG. 7, a wavefront required for the irradiation light is preferably obtained using the above-described backpropagation analysis. An aberration correction hologram is preferably obtained on the basis of the wavefront.

As a method of correcting the aberration caused by the surface shape of the biological sample B, for example, a method of combining a phase modulator (mainly, a deformable mirror) with a wavefront measurement device (a Shack-Hartmann sensor) and embedding fluorescent beads with a known size or shape at a particular position inside the biological sample B can be considered. In this method, excitation light and fluorescence from the fluorescent beads are both under an influence of aberration. Therefore, the aberration is measured by measuring a fluorescence intensity distribution using the wavefront measurement device. A hologram for correcting the aberration is presented to the phase modulator. In this case, the fluorescent beads are used as reference information.

However, in such a method, it is necessary for fluorescent beads to be embedded by surgery, and this method is not applicable in a case in which it is difficult to embed the fluorescent beads or a state of the biological sample B being changed due to the embedded fluorescent beads. On the other hand, according to the method of this embodiment, it is not necessary to embed the fluorescent beads.

Further, a method of obtaining an aberration correction hologram by trial and error by presenting a plurality of holograms by which an aberration is assumed to be reduced to a spatial light modulator, scanning the irradiation light modulated by the spatial light modulator, and selecting a hologram by which luminance or resolution of an obtained image is improved may be considered.

However, such a method takes a long time to repeat an experiment and design. Further, the obtained aberration correction hologram is likely to be an approximate solution, and accuracy is suppressed to be low. On the other hand, in the method of this embodiment, since the calculation of the aberration correction hologram data is all performed in the computer 43, it is possible to shorten the required time as compared with the method with trial and error of an operator. Further, in the method of this embodiment, since the computer 43 generates the aberration correction hologram data on the basis of the information on the surface shape acquired in the shape measurement unit 20, it is possible to enhance accuracy of the aberration correction.

Further, a method of correcting an aberration by causing the fluorescence generated in the biological sample B to separate, condensing one of the separated fluorescences using a lens, and imaging a condensing image using the camera may also be considered (see Patent Literature 1). The condensing image becomes a diffraction limited image when there is no aberration caused by the surface shape of the biological sample B, whereas the condensing image has a shape with distortion when there is an aberration. Therefore, in this method, a plurality of aberration conditions according to the shape of a plurality of condensing images are stored in advance, and an appropriate condition is selected from among the conditions to perform aberration correction.

However, in such a method, the obtained aberration correction hologram is highly likely to be an approximate solution, and accuracy is suppressed to be low. In the method of this embodiment, since the computer 43 generates the aberration correction hologram data on the basis of information on the surface shape acquired in the shape measurement unit 20, it is possible to enhance accuracy of aberration correction.

The hologram presented to the first spatial light modulator 33 and the second spatial light modulator 36 may not be the aberration correction hologram itself. For example, the hologram may be a hologram in which another hologram such as a hologram for controlling a condensing shape or a focus position of the irradiation light L1 with which the biological sample B is irradiated is superimposed on the aberration correction hologram.

Second Embodiment

In the first embodiment, the correction of the aberration caused by the surface shape of the biological sample B has been described, but an aberration may be caused by an internal structure directly under the surface of the biological sample B. Hereinafter, such a phenomenon will be described in detail.

Even when the biological sample B is irradiated with irradiation light with a certain light intensity, the fluorescence intensity to be observed is different between a deep position and a shallow position in the biological sample B. This is due to scattering and an aberration of the irradiation light or fluorescence caused by an internal structure of the biological sample B. One cause of occurrence of the scattering or the aberration is a change in the optical path caused by a refractive index difference between organs constituting, macroscopically, a structure of a blood vessel or the like and, microscopically, a cell. In particular, at a deep position in the biological sample B, the optical path is changed due to the internal structure, and a condensing shape of the irradiation light is greatly changed. Thus, a decrease in the fluorescence intensity and the resolution which is observed and a decrease in an S/N ratio due to background noise occur.

Therefore, in this embodiment, an internal structure with a refractive index difference directly under the surface of the biological sample B is measured, and a hologram including an aberration correction hologram for correcting an aberration caused by the internal structure is presented to the first spatial light modulator 33 and the second spatial light modulator 36. Thus, a decrease in strength and resolution of the light to be detected L2 and a decrease in the S/N ratio due to background noise can be suppressed.

Figure 8:
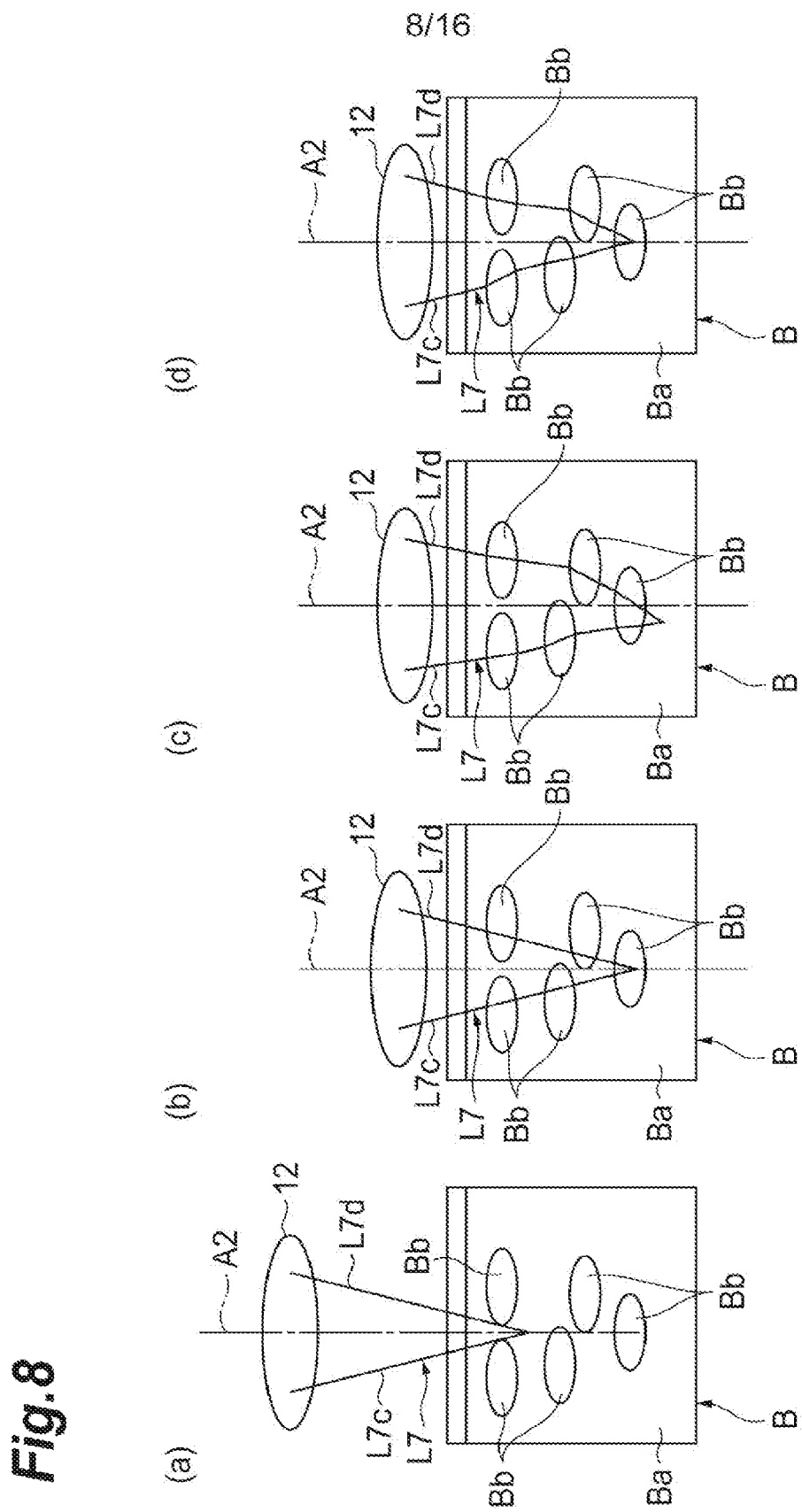
FIGS. 8(a) to 8(d) are diagrams when a biological sample is viewed from the side, and conceptually illustrate a state in which irradiation light is condensed while passing through an internal structure including media with different refractive indexes.

FIGS. 8(a) to 8(d) are diagrams when the biological sample B is viewed from the side, and schematically illustrate a state in which irradiation light is condensed while passing through an inner structure including media Ba and Bb with different refractive indexes. FIGS. 8(a) and 8(b) illustrate a state of condensing of irradiation light L7 when no aberration is assumed, and the irradiation light L7 is condensed in a shallow position and a deep position in the biological sample B. As illustrated in FIG. 8(a), when the irradiation light L7 is condensed in the shallow position, the boundary of the refractive index present on the optical path is relatively small. On the other hand, as illustrated in FIG. 8(b); when the irradiation light L7 is condensed in the deep position, the boundary of the refractive index present on the optical path increases. Therefore, in such a case, the irradiation light is actually influenced by the internal structure of the biological sample B, as illustrated in FIG. 8(c).

When the aberration correction is not performed as in FIG. 8(c), rays L7c and L7d near a lens outer peripheral portion are refracted under an influence of the internal structure. On the other hand, since a refraction angle of rays near the optical axis A2 is small, the rays near the optical axis A2 are less affected by the internal structure. As a result, a focus position of the rays near the optical axis A2 is different from a focus position of the rays L7c and L7d, and an aberration occurs. FIG. 8(d) illustrates a case in which such an aberration has been corrected. By correcting the wavefront of the irradiation light L7 in consideration of the refractive index distribution of the internal structure, the focus position of the rays near the optical axis A2 matches the focus position of the rays L7c and L7d, and condensing of the irradiation light L7 can be achieved at high density.

Figure 9:
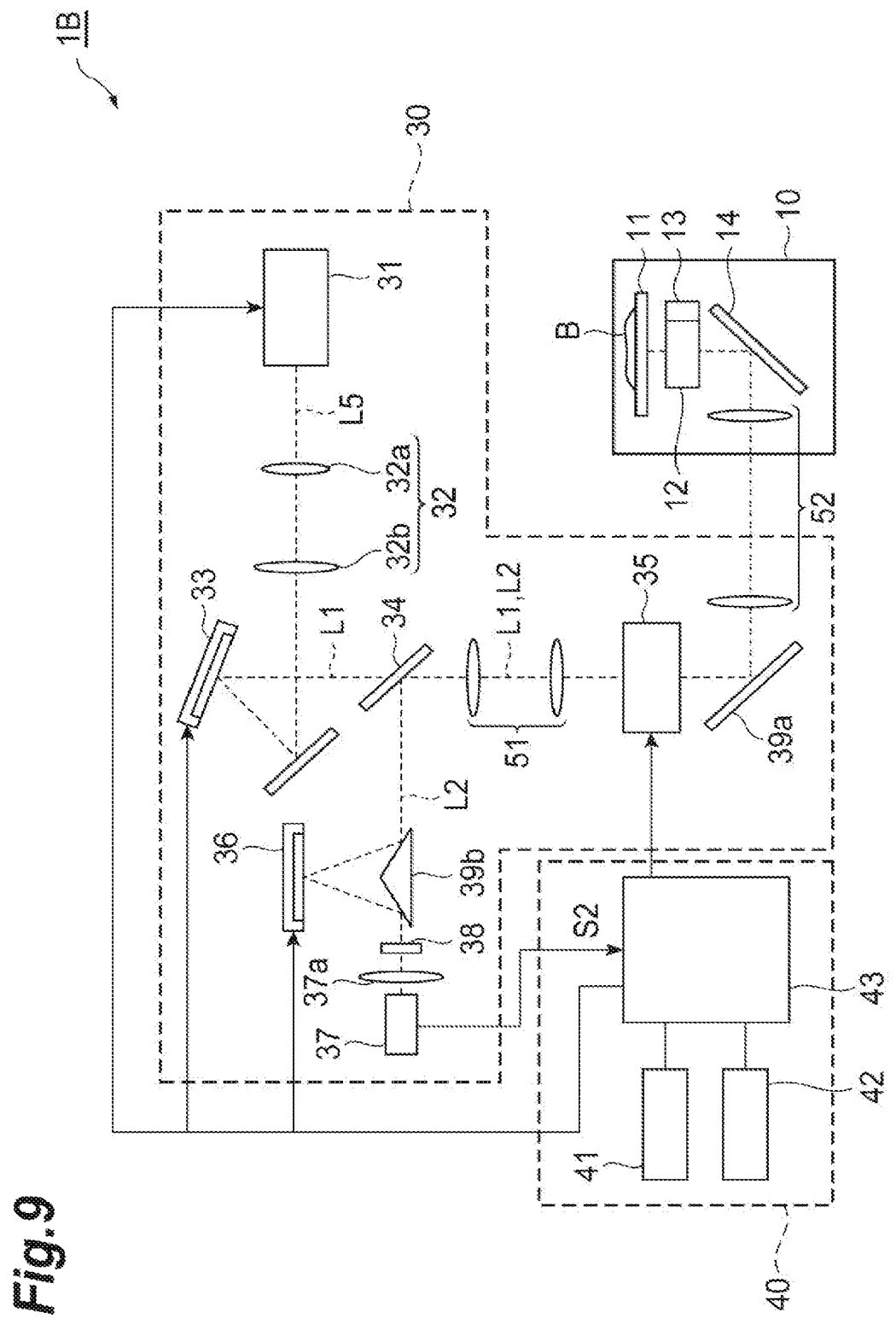
FIG. 9 is a diagram illustrating a configuration of a microscope apparatus of a second embodiment.

FIG. 9 is a diagram illustrating a configuration of a microscope apparatus 1B of this embodiment. A difference between the microscope apparatus 1B and the microscope apparatus 1A of the first embodiment is presence or absence of the shape measurement unit 20. That is, the microscope apparatus 1B of this embodiment does not include the shape measurement unit 20 and, instead, the objective lens moving mechanism 13 of the microscope unit 10 and the laser light source 31, the optical scanner 35, and the detector 37 of the image acquisition unit 30 constitute a shape acquisition unit that acquires information on the internal structure directly under the surface of the biological sample B. In this embodiment, the computer 43 acquires information on the internal structure of the biological sample B on the basis of a detection signal S2 Obtained by moving the objective lens 12 in the optical axis direction. The image acquisition unit 30 includes the detector 37 and is optically coupled to the objective lens 12.

With the configuration of this embodiment, it is possible to acquire information on the internal structure directly under the surface of the biological sample B. That is, when a suitable fluorescent material is used, information on the internal structure of the biological sample B is included in the obtained fluorescence image. Therefore, a distance between the objective lens 12 and the biological sample B is sequentially changed using the objective lens moving mechanism 13. When the irradiation light (excitation light) L1 is condensed at a deep position inside the biological sample B, fluorescence (including autofluorescence) is emitted from a structure inside the biological sample B present on the optical path of the irradiation light (excitation light) L1. Accordingly, it is possible to recognize a refractive index distribution of the biological sample B by acquiring the fluorescence intensity while setting a focus position shallower. It is possible to reduce an influence of an aberration by presenting the aberration correction hologram taking the recognized refractive index distribution into account to the first spatial light modulator 33 and the second spatial light modulator 36.

In this embodiment, the biological sample B may be a sample that emits fluorescence from a specific portion due to a fluorescent dye, a fluorescent protein, autofluorescence, or Second Harmonic Generation (SHG), or the like. Further, in the following description, the operation for measurement of the internal structure as described above using the objective lens moving mechanism 13, the laser light source 31, the optical scanner 35, and the detector 37 is referred to as pre-scan.

In a laser scanning fluorescence microscope such as the microscope apparatus 1B, scanning is performed by the optical scanner 35 (for example, an XY galvanometer) in order to observe the fluorescent image within a plane perpendicular to the optical axis. Information within a plurality of planes with different depths is obtained through a movement of the objective lens 12 or the biological sample table 11 in the optical axis direction. Finally, three-dimensional information is constructed by combining the information.

Further, the shape acquisition unit may measure the refractive index distribution using light sheet light used for fluorescence observation of a single photon, ultrasound, or the like, in place of the above configuration or together with the above configuration. Thus, it is possible to recognize a rough structure before observation in advance and preferably design an aberration correction hologram for correcting an aberration caused by the structure.

Figure 10:
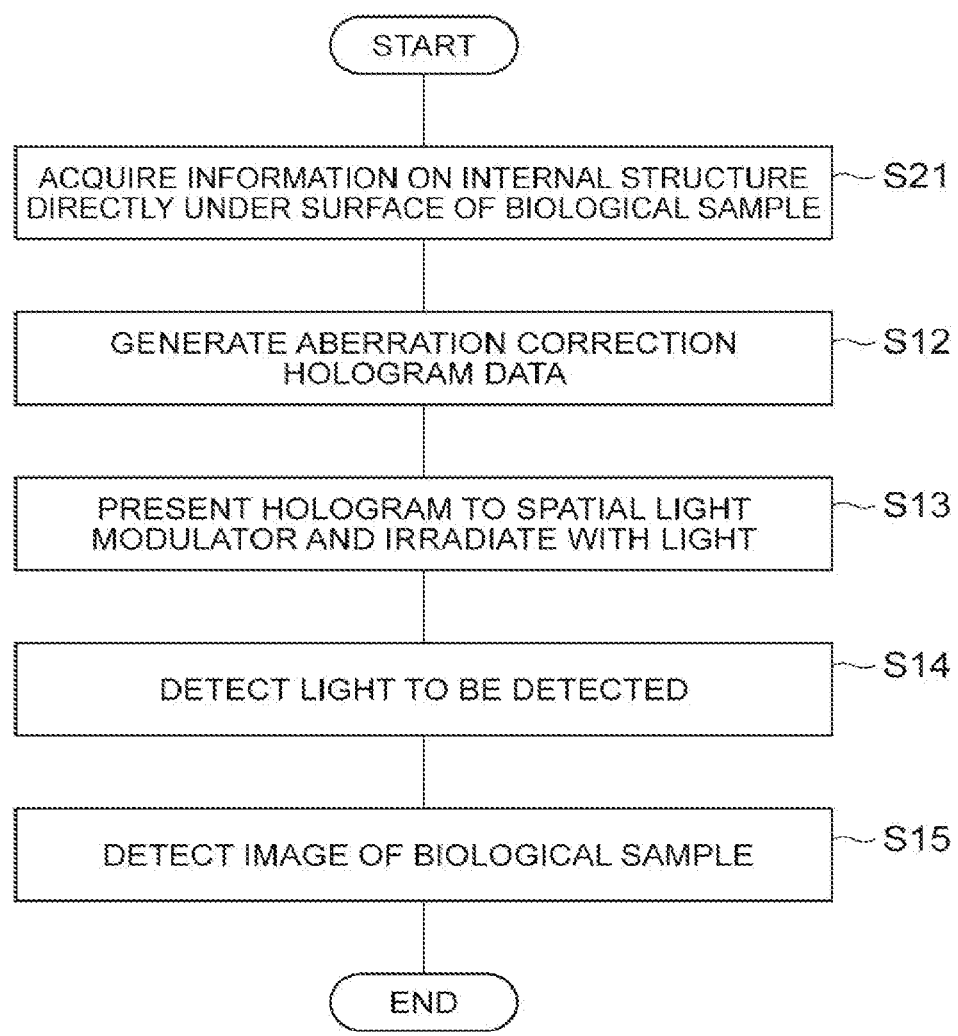
FIG. 10 is a flowchart illustrating an operation of a microscope apparatus and an image acquisition method according to this embodiment.

FIG. 10 is a flowchart illustrating an operation of the microscope apparatus 1B described above, and an image acquisition method according to this embodiment. First, the biological sample B is placed on the biological sample table 11. Then, a focus position is gradually moved from a shallow position in the biological sample B to a deep position while moving the objective lens 12 in an optical axis direction. At the same time, the light L5 is output from the laser light source 31 and the irradiation light L1 is condensed directly under the surface of the biological sample B. Thus, in the internal structure directly under the surface of the biological sample B, the light to be detected (fluorescence) L2 is generated. The light to be detected L2 is descanned by the optical scanner 35 and reflected by the dichroic mirror 34. The detector 37 detects the descanned light to be detected L2, and outputs the detection signal S2.

In this case, the aberration correction is not performed by the first spatial light modulator 33. Thus, a change in fluorescence in a depth direction caused by the internal structure directly under the surface of the biological sample B is detected. This operation is performed repeatedly while moving the optical axis of the irradiation light L1 using the optical scanner 35. Accordingly, three-dimensional information on the internal structure of the biological sample B is constructed. A refractive index distribution is estimated from the constructed three-dimensional information (shape acquisition step S21).

Thereafter, the hologram generation step S12, the light irradiation step S13, the light detection step S14, and the image generation step S15 are performed, similar to the first embodiment. In the observations at a deep position, since the irradiation light L1 and the light to be detected L2 pass through a portion or all of the estimated refractive index distribution, an aberration correction hologram may be generated so that an influence of the refractive index distribution on the irradiation light L1 and the light to be detected L2 passing through the refractive index distribution is reduced in the hologram generation step S12. In this embodiment, the aberration correction hologram is designed on the basis of a wavefront obtained through backpropagation using geometrical optics, wave optics, electromagnetic field analysis, or the like. The geometrical optics is, for example, backward ray tracing, the wave optics is, for example, Fresnel wavefront propagation or Fresnel Kirchhoff diffraction, and the electromagnetic field analysis is, for example, FDTD or RCWA.

Although the aberration correction hologram is generated on the basis of the surface shape of the biological sample B in the first embodiment, and the aberration correction hologram is generated on the basis of the structure with a refractive index distribution directly under the surface of the biological sample B in the second embodiment, the aberration correction hologram may be generated on the basis of both of the surface shape of the biological sample B and the structure directly under the surface of the biological sample B.

Further, although the shape acquisition unit of this embodiment acquires the information on the structure directly under the surface of the biological sample B using fluorescence obtained by radiating the irradiation light L1, the shape acquisition unit may measure the refractive index distribution directly under the surface of the biological sample B using ultrasound or may measure the refractive index distribution directly under the surface using a phase difference or a differential interference. Alternatively, the shape acquisition unit may change an angle of the optical axis or change a refractive index of an immersion liquid and estimate the refractive index distribution or a scattering degree directly under the surface from reflection, transmission, or the like. Accordingly, it is possible to estimate, particularly, the refractive index distribution in the surface of the biological sample B. For example, when the angle of the optical axis is changed, the refractive index of the surface of the biological sample B or the refractive index distribution inside the sample can be estimated from a Brewster angle or a relationship between the angle and a reflectance.

Effects obtained by the microscope apparatus 1B and the image acquiring method having the above configuration of this embodiment will be described. In the microscope apparatus 1B and the image acquiring method of this embodiment, the information on the internal structure directly under the surface of the biological sample B is acquired. On the basis of this information, the aberration correction hologram data for correcting the aberration is generated. Further, the irradiation light L1 is modulated using the hologram based on the data. Thus, since the aberration caused by the internal structure directly under the surface of the biological sample B is preferably corrected, it is possible to suppress a decrease in the condensing intensity of the irradiation light L1 and spreading of the condensing shape inside the biological sample B.

Further, in this embodiment, the hologram based on the aberration correction hologram data may be presented to the second spatial light modulator 36, and the light to be detected L2 generated in the biological sample B may be modulated by the second spatial light modulator 36. Thus, since an influence of the aberration caused by the internal structure directly under the surface of the biological sample B on the light to be detected L2 is corrected, a clearer image of the biological sample B can be obtained.

First Modification Example

Figure 11:
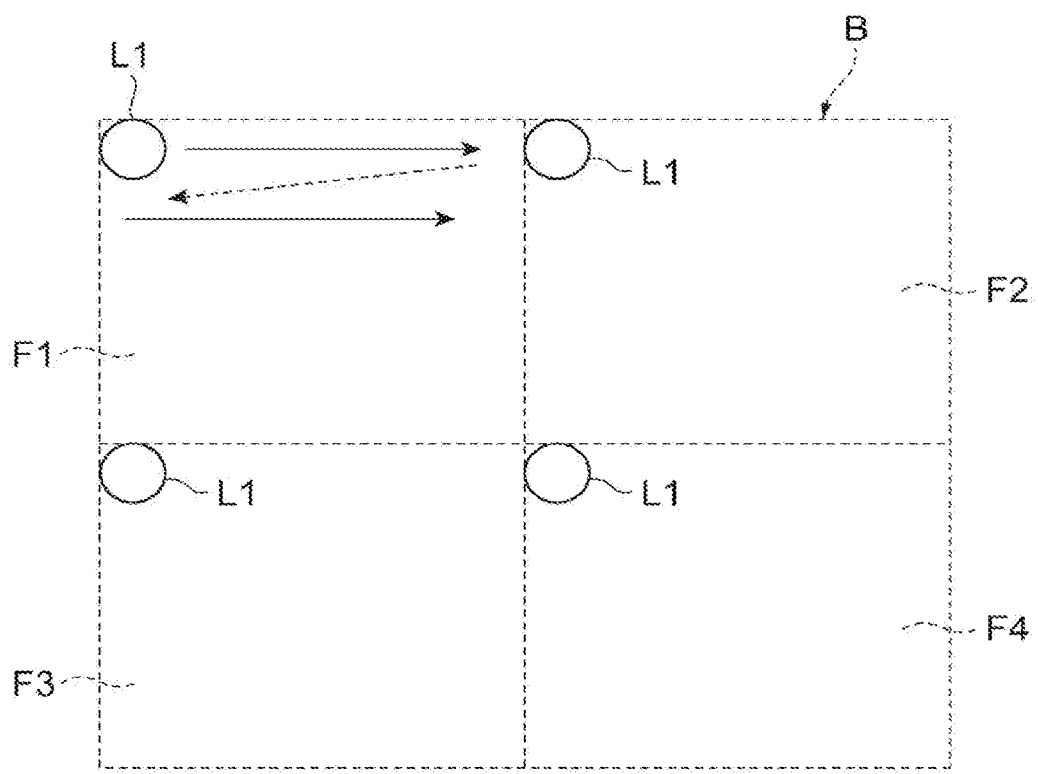
FIG. 11 is a diagram illustrating an operation of a first modification and is a diagram when a surface of a biological sample is viewed in an optical axis direction.

FIG. 11 is a diagram illustrating an operation of a first modification example, and is a diagram when the surface of the biological sample B is viewed in the optical axis direction. In the second embodiment, the shape acquisition unit may divide a surface of the biological sample B into a plurality of regions F1 to F4 in a grid pattern as illustrated in FIG. 11 and perform scanning in small areas in parallel in the respective regions F1 to F4 (in the shape acquisition step). In this case, an individual aberration correction hologram is generated for each of the regions F1 to F4, and a hologram having effects of aberration correction and multi-point generation is presented to the first spatial light modulator 33.

FIGS. 12(a) and 12(b) are diagrams illustrating examples of a boundary B1 at the outer side of the biological sample B. Since a distance between the objective lens 12 and the boundary B1 and an internal structure directly under the surface of the biological sample B greatly change when the irradiation light L1 scans a wide region as illustrated in FIG. 12(a), an aberration correction hologram may be switched midway. However, in this case, a loss of time is caused by a slow operation of the spatial light modulator. On the other hand, when a size of the scanning region is reduced through division into a plurality of regions F1 to F4 as illustrated in FIG. 12(b), it is not necessary to switch the aberration correction hologram, and high-accuracy and high-speed scanning are realized.

Second Modification Example

Figure 13:
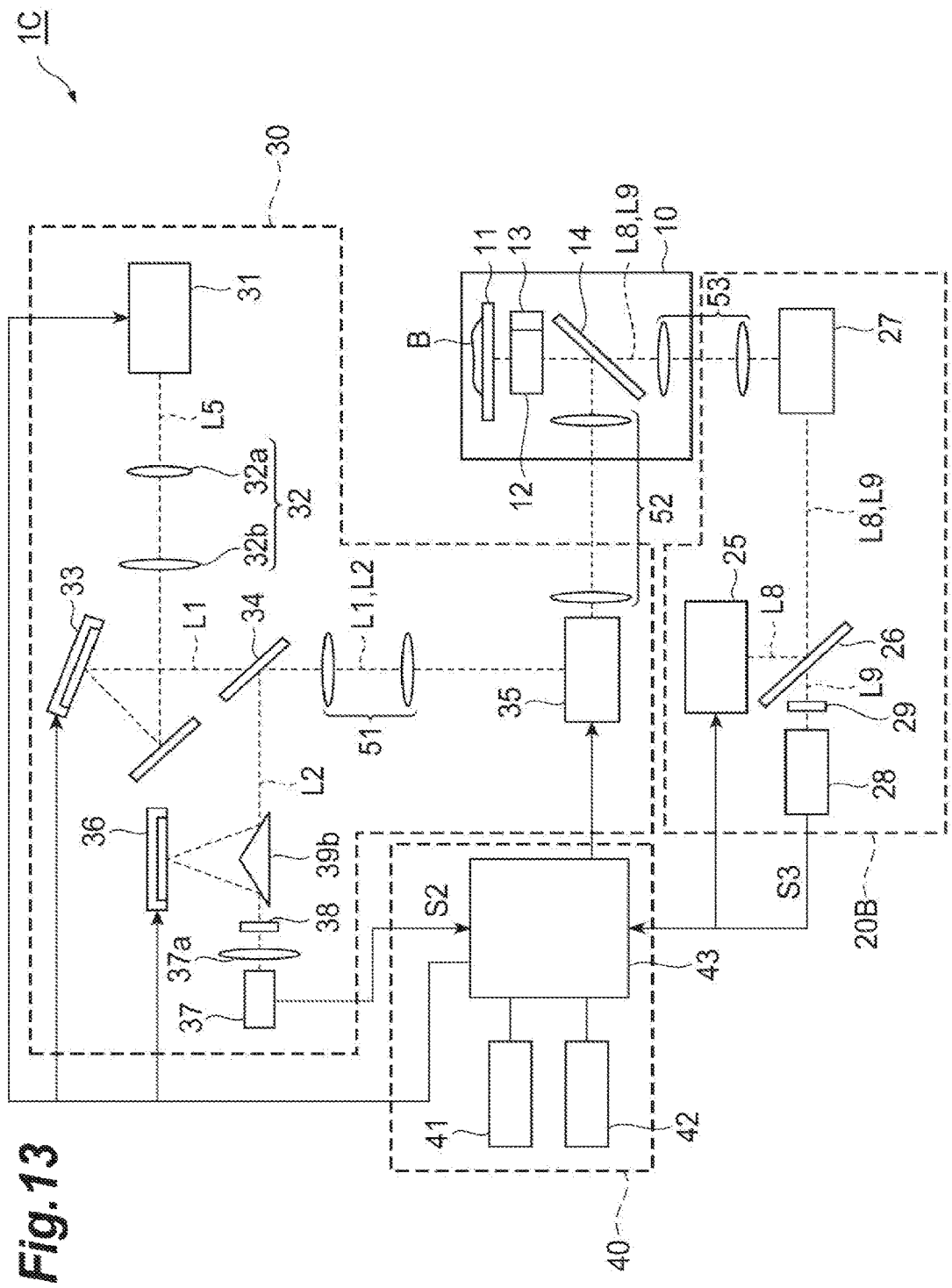
FIG. 13 is a diagram illustrating a configuration of a microscope apparatus according to a second modification example.

FIG. 13 is a diagram illustrating a configuration of a microscope apparatus 1C according to a second modification example. In the microscope apparatus 1C of this modification example, a shape measurement unit 20B constitutes the shape acquisition unit. The shape measurement unit 20B includes a light source 25, a dichroic mirror 26, an optical scanner 27, a detector 28, and a filter 29. The shape measurement unit 20B includes a detector 28 and is optically coupled to an objective lens 12.

The light source 25 outputs excitation light L8 with which a biological sample B is irradiated. In this modification example, the biological sample B may be a sample that emits fluorescence from a specific portion due to a fluorescent dye, a fluorescent protein, autofluorescence, SHG, or the like, similar to the second embodiment. Then, the excitation light L8 is light including a wavelength that excites the biological sample B. The excitation light L8 may be light with the same wavelength as the light L5 output from the laser light source 31 or may be light with a wavelength different from that of the light L5 output from the laser light source 31.

The dichroic mirror 26 transmits one of the excitation light L8 from the light source 25 and fluorescence L9 from the microscope unit 10, and reflects the other. In the example illustrated in FIG. 13, the dichroic mirror 26 reflects the excitation light L8 and transmits the fluorescence L9.

The optical scanner 27 scans an irradiation position of the excitation light L8 in the biological sample B by moving an optical axis of the excitation light L8 within a plane perpendicular to the optical axis of the excitation light L8. The optical scanner 27 includes, for example, a galvanometer mirror, a resonant mirror, or a polygon mirror. The fluorescence L9 from the biological sample B is detected through the optical scanner 27. Thus, it is possible to match the optical axis of the excitation light L8 with the optical axis of the fluorescence L9.

The detector 28 detects a light intensity of the fluorescence L9 output from the biological sample B via the objective lens 12, and outputs a detection signal S3. The detector 28 may be a point sensor such as a PMT, a photodiode, or an avalanche photodiode. Alternatively, the detector 28 may be an area image sensor such as a CCD image sensor, a CMOS image sensor, a multi-anode PMT, or a photodiode array. A confocal effect may be imparted due to a pinhole disposed at a preceding stage from the detector 28.

The filter 29 is disposed on an optical axis between the dichroic mirror 26 and the detector 28. The filter 29 cuts a wavelength of the excitation light L8 and a wavelength of fluorescence or the like unnecessary for observation from the light that is input to the detector 28.

When a distance between the objective lens 12 and the light source 25 is long, at least one 4f optical system may be provided on an optical axis of the excitation light L8 and the fluorescence L9. As an example, one 4f optical system 53 is illustrated in FIG. 13. The 4f optical system 53 is disposed on the optical axis between the optical scanner 27 and the beam splitter 14.

In this modification, first, the biological sample B is placed on the biological sample table 11. Then, a focus position is gradually moved from a shallow position in the biological sample B to a deep position while moving the objective lens 12 in an optical axis direction. At the same time, the light L8 is output from the laser light source 25 and fluorescence L9 from the internal structure directly under the surface of the biological sample B is detected in the detector 28. Thus, a change in the fluorescence in a depth direction caused by the internal structure directly under the surface of the biological sample B is detected. This operation is repeatedly performed while moving the optical axis of the excitation light L8 using the optical scanner 27. Accordingly, three-dimensional information on the internal structure of the biological sample B is constructed. A refractive index distribution is estimated from the constructed three-dimensional information. A subsequent operation is the same as in the second embodiment described above. When a wavelength of the excitation light L8 is included in wavelengths of the light L5 output from the laser light source 31, the functions of the light source 25 and the optical scanner 27 may be realized by the laser light source 31 and the optical scanner 35. In this case, the light source 25, the optical scanner 27, and the beam splitter 26 are not necessary.

Third Modification Example

In the second embodiment described above, pre-scan may be repeated a plurality of times, and in the second and subsequent pre-scans, an aberration of light L5 may be corrected by the first spatial light modulator 33 on the basis of a previous pre-scan result. Thus, when the biological sample B is irradiated with the light L5, it is possible to reduce an influence of an aberration caused by the internal structure of the biological sample B, more accurately recognize a structure of the biological sample B, and obtain a higher resolution image.

Specifically, in first pre-scan, the irradiation light L1 becomes plane waves since the aberration correction is not performed, but in second pre-scan, a wavefront for correcting the aberration is applied to the irradiation light L1. The aberration correction hologram is designed on the basis of a structure of the biological sample B obtained by the second and subsequent pre-scans. Alternatively, rough aberration correction may be performed by the first pre-scan, and finer aberration correction may be performed by the second and subsequent pre-scans.

Fourth Modification Example

Figure 14:
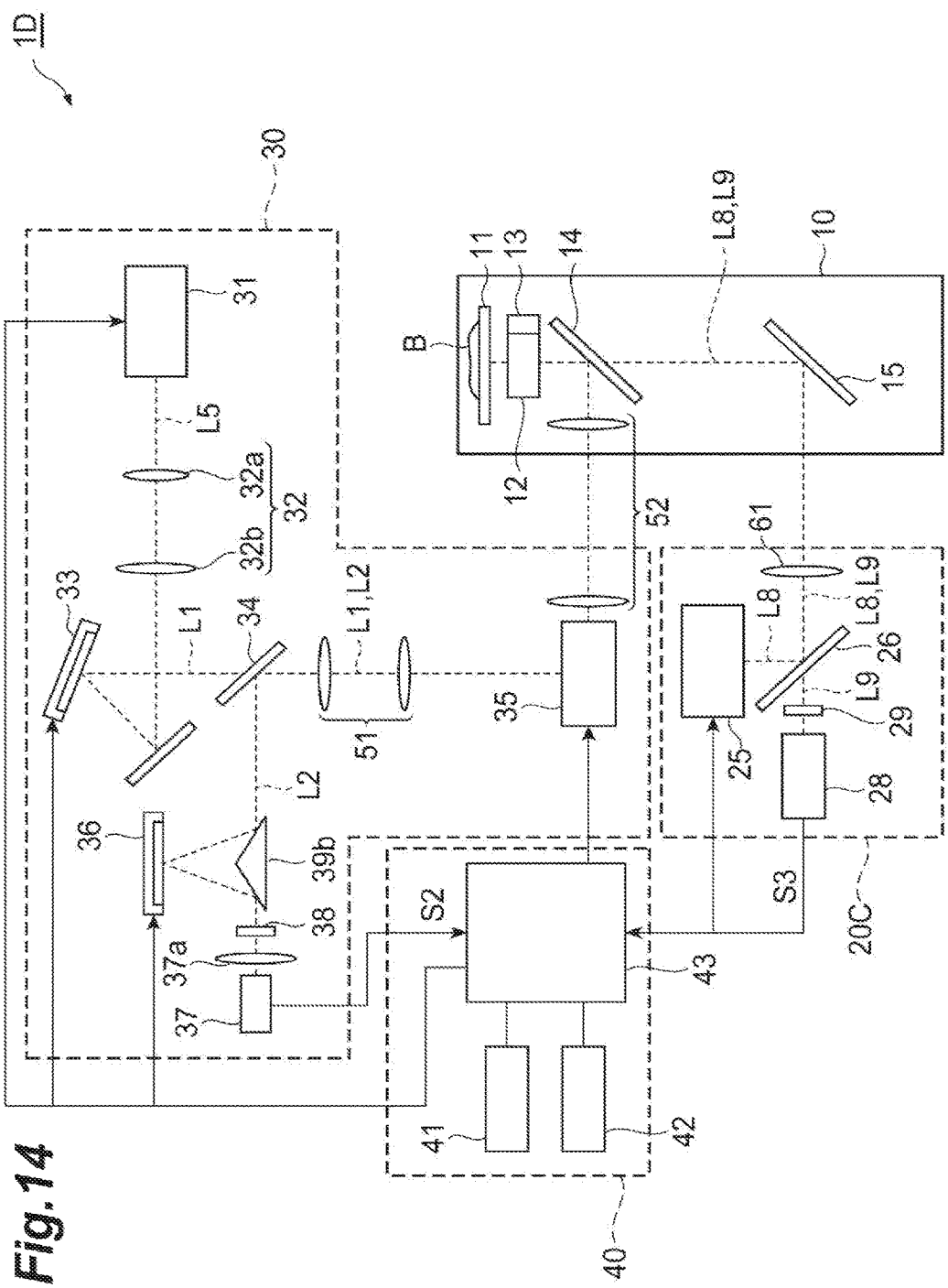
FIG. 14 is a diagram illustrating a configuration of a microscope apparatus according to a fourth modification example.

FIG. 14 is a diagram illustrating a configuration of a microscope apparatus 1D according to a fourth modification. In this modification example, an evanescent field is used for measurement of the surface shape of the biological sample B. Accordingly, shape recognition such as recognition as to whether or not the biological sample B is grounded to the biological sample table 11 is facilitated. In this modification example, the objective lens 12 and the biological sample table 11 (cover glass) in which total reflection occurs are used in order to generate an evanescent field.

In the microscope apparatus 1D of this modification example, the shape measurement unit 20C constitutes a shape acquisition unit. The shape measurement unit 20C includes a light source 25, a dichroic mirror 26, a detector 28, a filter 29, and a condensing lens 61. Configurations of the light source 25, the dichroic mirror 26, the detector 28, and the filter 29 are the same as those in the third modification example. The shape measurement unit 20C is optically coupled to the objective lens 12.

The condensing lens 61 is provided when the excitation light L8 is a surface illumination, and is disposed on the optical axis between the dichroic mirror 26 and the microscope unit 10. The condensing lens 61 condenses the excitation light L8 on a rear focal plane of the objective lens 12. When the excitation light L8 is a point illumination, the condensing lens 61 is not necessary. In this case, for example, the excitation light L8 which is plane waves may be input to a region in which total reflection of the objective lens 12 occurs and the excitation light L8 may be scanned through parallel movement of the optical scanner or the biological sample table 11. Further, a prism or an optical fiber may be used in place of the objective lens 12.

Fifth Modification Example

Figure 15:
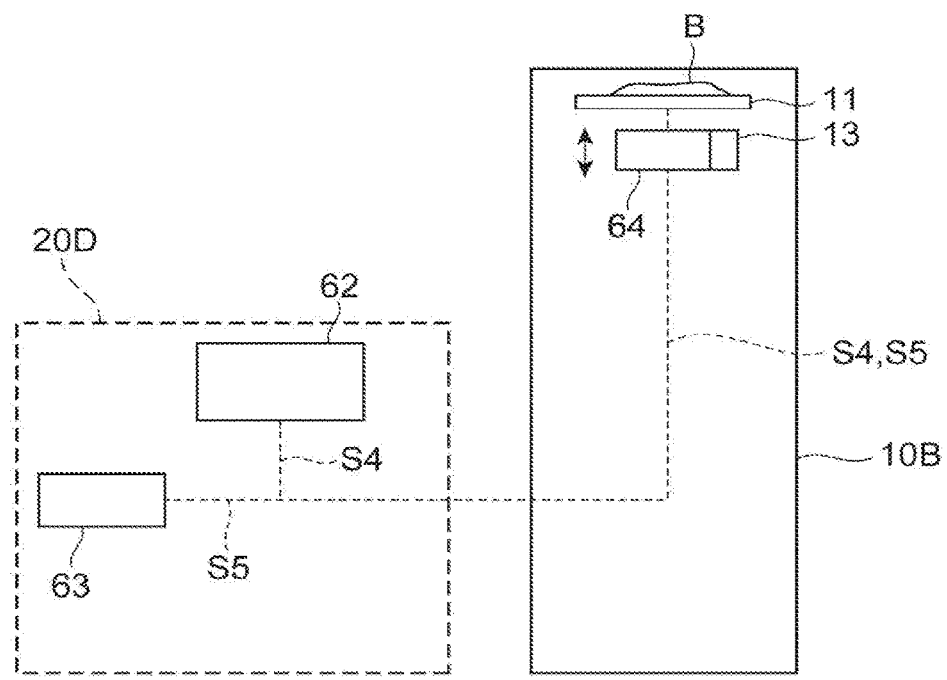
FIG. 15 is a diagram illustrating a configuration of a microscope unit and a shape measurement unit of a microscope apparatus according to a fifth modification.

FIG. 15 is a diagram illustrating a configuration of a microscope unit 10B and a shape measurement unit 20D of a microscope apparatus according to a fifth modification example. In this modification example, elasticity of the biological sample B is measured using ultrasound, and a structure of the biological sample B is obtained using an elasticity difference between regions of the biological sample B. An aberration correction hologram is generated on the basis of the obtained structure. The image acquisition unit 30 and the control unit 40 illustrated in FIGS. 1 and 9 are not illustrated in FIG. 15.

As illustrated in FIG. 15, the shape measurement unit 20D of this modification example includes a pulse generation source 62 and a receiver 63 which is a detector. The pulse generation source 62 generates a pulse signal S4 for generating ultrasound. The receiver 63 receives the pulse signal S5 including information on an internal structure of the biological sample B.

The microscope unit 10B includes a lens with a piezoelectric thin film 64 in place of the objective lens 12 of the microscope unit 10 illustrated in FIGS. 1 and 9. Other configurations are the same as those of the microscope unit 10. The lens with the piezoelectric thin film 64 is disposed to face the biological sample B, converts a pulse signal S4 to ultrasound using the piezoelectric thin film, irradiates the biological sample B with the ultrasound, and converts the ultrasound reflected in the biological sample B into a pulse signal S5. Although a common lens with a piezoelectric thin film is used for the pulse signal S4 and the pulse signal S5 in this modification example, a lens with a piezoelectric thin film for the pulse signal S4 and a lens with a piezoelectric thin film for the pulse signal S5 may be provided individually.

Sixth Modification Example

Figure 16:
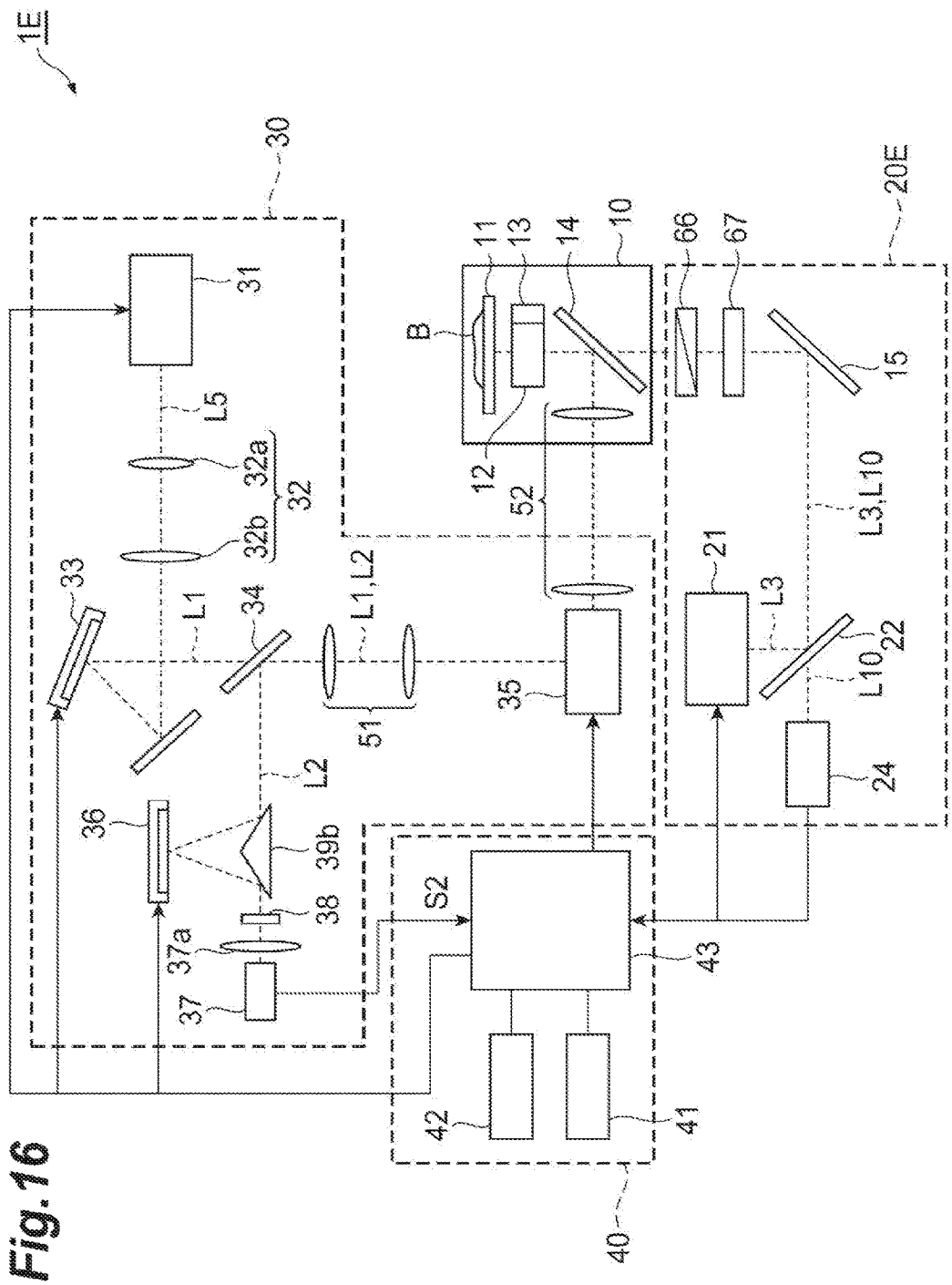
FIG. 16 is a diagram illustrating a configuration of a microscope apparatus according to a sixth modification example.

FIG. 16 is a diagram illustrating a configuration of a microscope apparatus 1E according to a sixth modification example. In this modification example, phase difference and differential interference are used for measurement of the surface shape of the biological sample B. In the microscope apparatus 1E of this modification example, the shape measurement unit 20E constitutes a shape acquisition unit. The shape measurement unit 20E includes a light source 21, a beam splitter 22, a detector 24, a differential interference (DIC) prism 66, and a polarizer 67. The shape measurement unit 20E is optically coupled to the objective lens 12. A configuration of the light source 21, the beam splitter 22, and the detector 24 is the same as that in the first embodiment.

The DIC prism 66 and the polarizer 67 are arranged side by side on the optical path between the beam splitter 22 and the objective lens 12. The DIC prism 66 causes the light L3 from the light source 21 to separate in two, and also superposes return light L10 from the biological sample B. The polarizer 67 limits the polarization of the lights L3 and L10. The light L10 reaching the beam splitter 22 from the biological sample B via the DIC prism 66 and the polarizer 67 is transmitted through the beam splitter 22 and input to the detector 24.

The microscope apparatus and the image acquisition method according to an aspect of the present invention are not limited to the above-described embodiments, and various modifications may be made. For example, although the aberration correction hologram is presented to the first spatial light modulator and the second spatial light modulator in the above embodiment, the aberration correction hologram may be presented to only the first spatial light modulator. In such a case, it is possible to suppress a decrease in the condensing intensity of the irradiation light inside the biological sample and spreading of the condensing shape. Further, although the case in which the microscope unit 10 is an inverted microscope has been described in the above embodiment, the microscope unit 10 may be an upright microscope.

The microscope apparatus according to the above embodiment is a microscope apparatus that acquires an image of a biological sample, and includes a biological sample table that supports the biological sample; an objective lens disposed to face the biological sample table; a light irradiation unit that irradiates the biological sample with light via the objective lens; a shape acquisition unit that acquires information on at least one of a surface shape of the biological sample and a structure directly under the surface of the biological sample; a hologram generation unit that generates aberration correction hologram data for correcting an aberration caused by the at least one on the basis of the information acquired in the shape acquisition unit; a spatial light modulator to which a hologram based on the aberration correction hologram data is presented and that modulates the light with which the biological sample is irradiated from the light irradiation unit; a photodetector that detects an intensity of light generated in the biological sample; and an image generation unit that generates an image of the biological sample on the basis of an output from the photodetector.

Further, an image acquisition method according to the above embodiment is a method of acquiring an image of a biological sample and includes a shape acquisition step of acquiring information on at least one of a surface shape of the biological sample supported by a biological sample table facing an objective lens and a structure directly under the surface of the biological sample; a hologram generation step of generating aberration correction hologram data for correcting an aberration caused by the at least one on the basis of the information acquired in the shape acquisition step; a light irradiation step of presenting a hologram based on the aberration correction hologram data to a spatial light modulator, modulating the light output from a light irradiation unit using the spatial light modulator, and irradiating the biological sample with light after modulation; a light detection step of detecting an intensity of light generated in the biological sample; and an image generation step of generating an image of the biological sample on the basis of detection information in the light detection step.

Further, the microscope apparatus according to the above embodiment is an apparatus that acquires an image of a biological sample, and includes a biological sample table that supports the biological sample; an objective lens disposed to face the biological sample table; a light source that outputs light with which the biological sample is irradiated via the objective lens; a shape acquisition unit that acquires information on at least one of a surface shape of the biological sample and a structure directly under the surface of the biological sample; a hologram generation unit that generates aberration correction hologram data for correcting an aberration caused by the at least one on the basis of the information acquired by the shape acquisition unit; a spatial light modulator to which a hologram based on the aberration correction hologram data is presented and that modulates the light output from the light source; a photodetector that detects an intensity of light generated in the biological sample and outputs a detection signal; and an image generation unit that generates an image of the biological sample on the basis of the detection signal.

Further, the image acquiring method according to the above embodiment is a method of acquiring an image of a biological sample and includes a shape acquisition step of acquiring information on at least one of a surface shape of the biological sample supported by a biological sample table facing an objective lens and a structure directly under the surface of the biological sample; a hologram generation step of generating aberration correction hologram data for correcting an aberration caused by the at least one on the basis of the information acquired in the shape acquisition step; a light irradiation step of presenting a hologram based on the aberration correction hologram data to a spatial light modulator, modulating the light output from a light source using the spatial light modulator, and irradiating the biological sample with light after modulation; a light detection step of detecting an intensity of light generated in the biological sample and outputting a detection signal; and an image generation step of generating an image of the biological sample on the basis of a detection signal in the light detection step.

Further, the microscope apparatus may be configured to further include a second spatial light modulator to which the hologram based on the aberration correction hologram data is presented and that modulates the light generated in the biological sample. Further, in the image acquiring method, the light detecting step may be configured to present the hologram based on the aberration correction hologram data to a second spatial light modulator, modulate the light generated in the biological sample using the second spatial light modulator, and detect an intensity of the light after modulation.

Accordingly, since an influence of an aberration caused by at least one of the surface shape of the biological sample and the structure directly under the surface of the biological sample on the light generated in the biological sample is corrected, a clear image of the biological sample can be obtained.

Further, an incoherent light source that outputs incoherent light may be used in place of the laser light source 31. The incoherent light source includes, for example, a super luminescent diode (SLD), a light emitting diode (LED), an Amplified Spontaneous Emission (ASE) light source, or a lamp-based light source.

INDUSTRIAL APPLICABILITY

One aspect of the present invention can be used as a microscope apparatus and an image acquisition method capable of suppressing a decrease in condensing intensity of irradiation light inside a biological sample and spreading of a condensing shape.

REFERENCE SIGNS LIST 1A to 1E: microscope apparatus
10 and 10B: microscope unit
11: biological sample table
12: objective lens
13: objective lens moving mechanism
14: beam splitter
15: reflective mirror
20, 20B to 20E: shape measurement unit
21: coherent light source
22: beam splitter
23: reference light mirror
24: detector
30: image acquisition unit
31: laser light source
32: beam expander
33: first spatial light modulator
34: dichroic mirror
35: optical scanner
36: second spatial light modulator
37: detector
40: control unit
A2: optical axis
B: biological sample
L1: irradiation light
L2: light to be detected
L3: coherent light
L4: interference light

The invention claimed is:
1. A microscope comprising:
a biological sample table configured to support a biological sample;
an objective lens disposed to face the biological sample table;
a light source configured to output light with which the biological sample is irradiated via the objective lens;
a computer configured to generate aberration correction hologram data for correcting an aberration caused by the at least one of a surface shape of the biological sample and a structure under the surface of the biological sample;
a spatial light modulator configured to modulate the light output from the light source based on the aberration correction hologram data; and
a photodetector configured to detect light generated in the biological sample and outputting a detection signal.

2. The microscope according to claim 1, further comprising:
an optical scanner configured to scan an irradiation position of the modulated light in the biological sample.

3. The microscope according to claim 2, wherein the photodetector is configured to detect the light through the optical scanner.

4. The microscope according to claim 1, wherein the photodetector is a point sensor.

5. The microscope according to claim 1, wherein the computer is configured to generate the aberration correction hologram data based on a refractive index distribution of the biological sample.

6. The microscope according to claim 1, further comprising:
a shape acquisition unit configured to acquire information on at least one of the surface shape of the biological sample and the structure under the surface of the biological sample.

7. A microscopy method comprising:
generating aberration correction hologram data for correcting an aberration caused by the at least one of a surface shape of the biological sample supported by a biological sample table facing an objective lens and a structure under the surface of the biological sample;
controlling a spatial light modulator based on the aberration correction hologram data, modulating light output from a light source using the spatial light modulator, and irradiating the biological sample with the modulated light; and
detecting light generated in the biological sample and outputting a detection signal.

8. The microscopy method according to claim 7, further comprising:
scanning an irradiation position of the modulated light in the biological sample.

9. The microscopy method according to claim 8, wherein the detecting detects the light through the light scanner.

10. The microscopy method according to claim 7, wherein the photodetector is a point sensor.

11. The microscopy method according to claim 7, wherein the generating generates the aberration correction hologram data based on a refractive index distribution of the biological sample.

12. The microscopy method according to claim 7, further comprising:
acquiring information on at least one of the surface shape of the biological sample and the structure under the surface of the biological sample.

* * * * *